(12) United States Patent
Liu et al.

(10) Patent No.: US 7,767,462 B2
(45) Date of Patent: Aug. 3, 2010

(54) ELECTROLYTIC ELUENT GENERATOR AND METHOD OF USE

(75) Inventors: Yan Liu, Santa Clara, CA (US); Nebojsa Avdalovic, Cupertino, CA (US)

(73) Assignee: Dionex Corporation, Sunnyvale, CA (US)

( * ) Notice: Subject to any disclaimer, the term of this patent is extended or adjusted under 35 U.S.C. 154(b) by 1127 days.

(21) Appl. No.: 11/417,832

(22) Filed: May 3, 2006

(65) Prior Publication Data

US 2006/0211125 A1    Sep. 21, 2006

Related U.S. Application Data

(62) Division of application No. 10/241,361, filed on Sep. 11, 2002, now Pat. No. 7,402,283.

(51) Int. Cl.
    *G01N 30/26* (2006.01)
(52) U.S. Cl. ............... 436/161; 422/70; 210/198.2; 210/656; 73/61.53; 73/61.55; 73/61.56
(58) Field of Classification Search ............ 436/150, 436/161, 174, 183; 422/72, 99, 82.02; 204/551, 204/647; 205/628, 633, 637; 210/656, 198.2; 73/61.53, 61.55, 61.56
    See application file for complete search history.

(56) References Cited

U.S. PATENT DOCUMENTS

| | | | |
|---|---|---|---|
| 5,045,204 A | 9/1991 | Dasgupta et al. | |
| 5,132,094 A | 7/1992 | Godec et al. | |
| 5,352,360 A | 10/1994 | Stillian et al. | |
| 5,567,293 A | 10/1996 | Paleologou et al. | |
| 5,961,796 A | 10/1999 | Hitchens et al. | |
| 6,027,643 A | 2/2000 | Small et al. | |
| 6,036,921 A | 3/2000 | Small et al. | |
| 6,224,731 B1 | 5/2001 | Mani | |
| 6,225,129 B1 | 5/2001 | Liu et al. | |
| 6,325,976 B1 | 12/2001 | Small et al. | |
| 6,607,921 B1 | 8/2003 | Hindsgaul et al. | |

FOREIGN PATENT DOCUMENTS

| | | |
|---|---|---|
| EP | 0941760 A1 | 9/1999 |
| GB | 2274409 A | 7/1994 |
| WO | WO 02/04940 A1 | 1/2002 |

*Primary Examiner*—Jan M Ludlow
(74) *Attorney, Agent, or Firm*—Morgan Lewis & Bockius LLP; David J. Brezner

(57) ABSTRACT

An acid or base is generated in an aqueous solution by the steps of:
  (a) providing a source of first ions adjacent an aqueous liquid in a first acid or base generation zone, separated by a first barrier (e.g., anion exchange membrane) substantially preventing liquid flow and transporting ions only of the same charge as said first ions,
  (b) providing a source of second ions of opposite charge adjacent an aqueous liquid in a second acid or base generation zone, separated by a second barrier transporting ions only of the same charge as the second ions, and
  (c) transporting ions across the first barrier by applying an electrical potential through said first and second zones to generate an acid-containing aqueous solution in one of said first or second zones and a base-containing aqueous solution in the other one which may be combined to form a salt. Also, electrolytic apparatus for performing the above method.

29 Claims, 15 Drawing Sheets

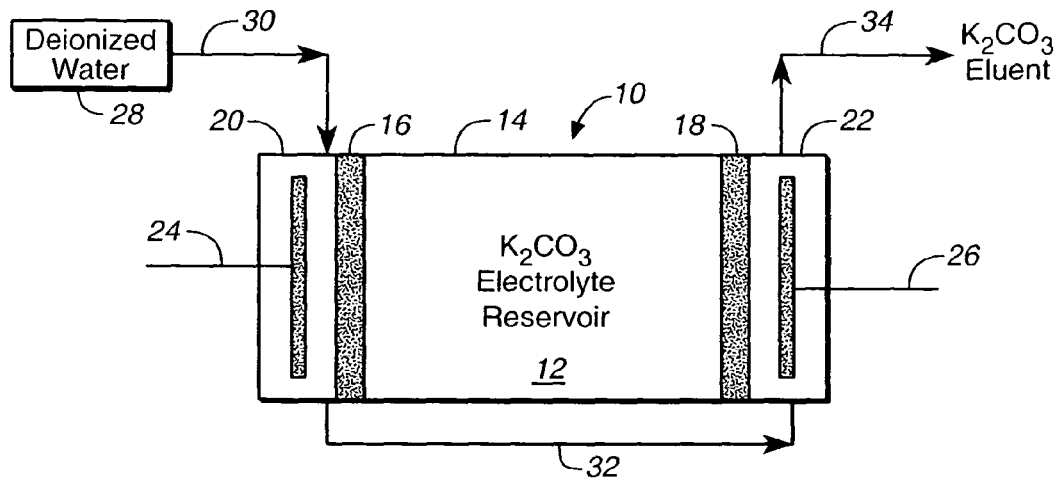
FIG._1
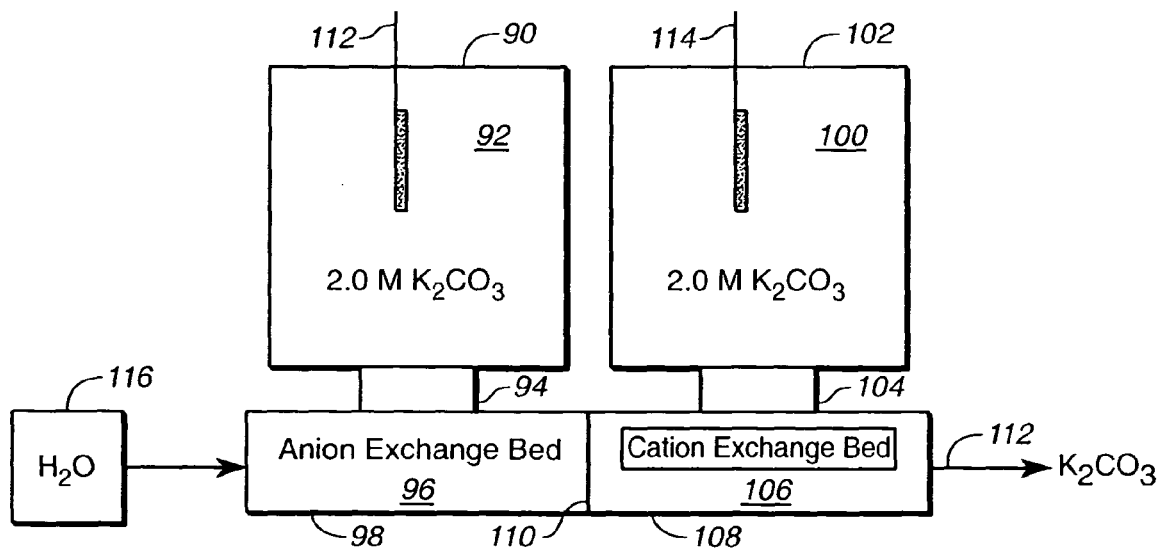
FIG._3

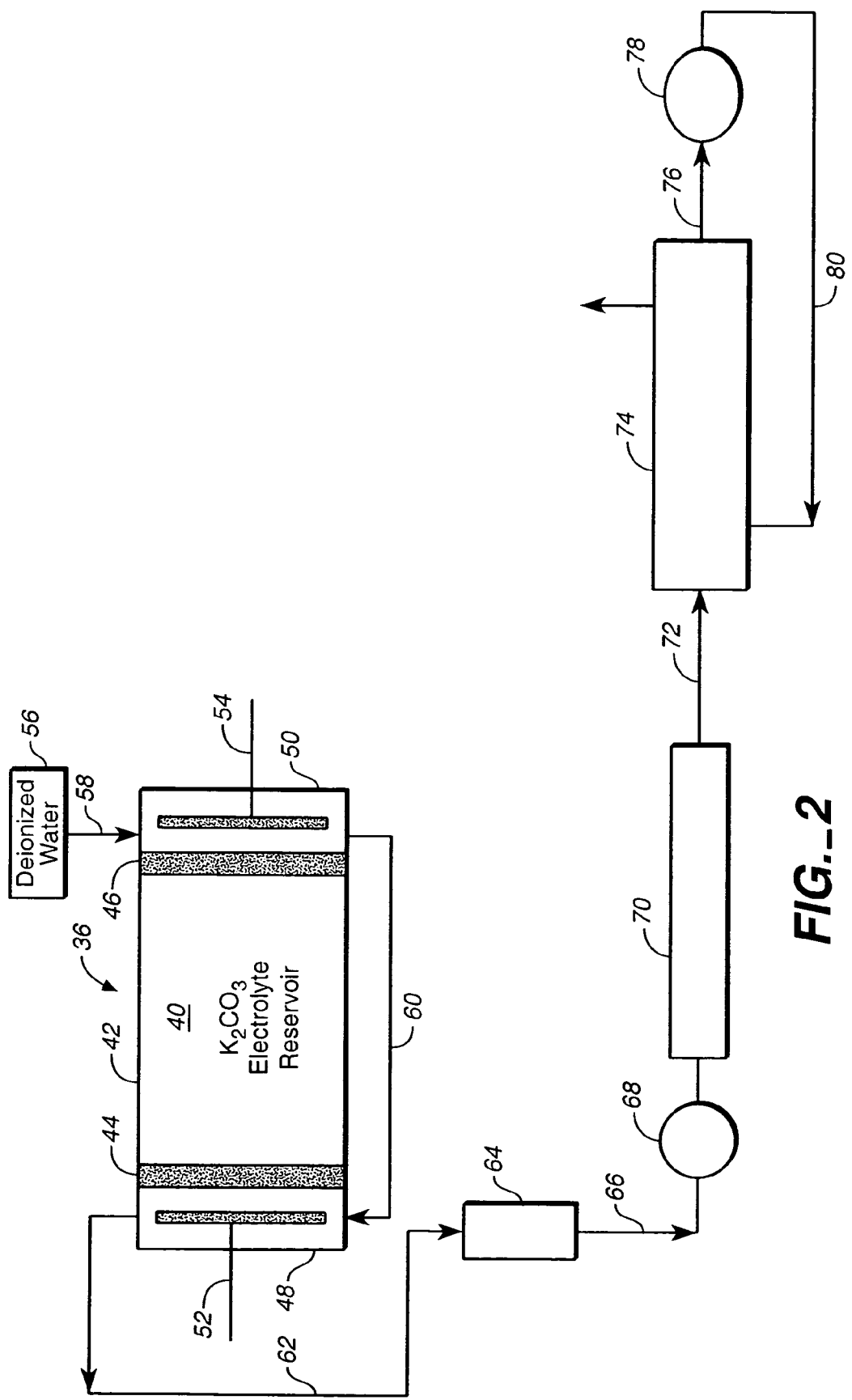
FIG._2

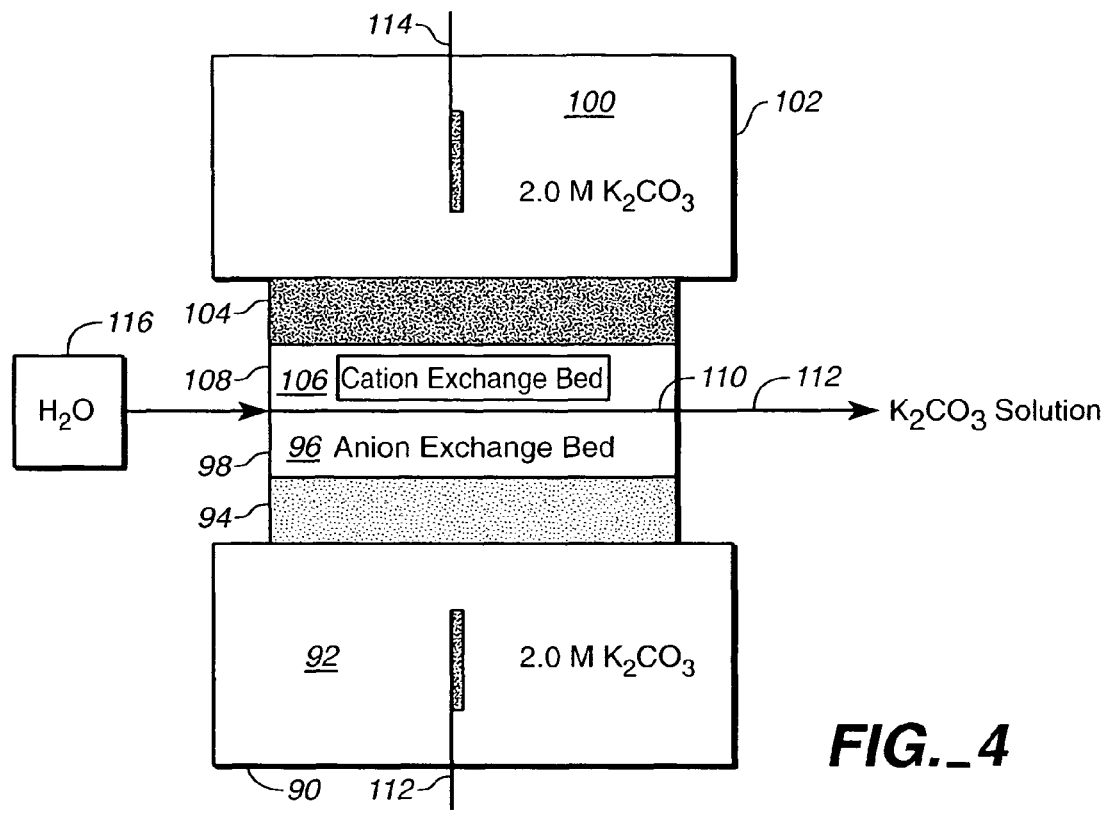
FIG._4
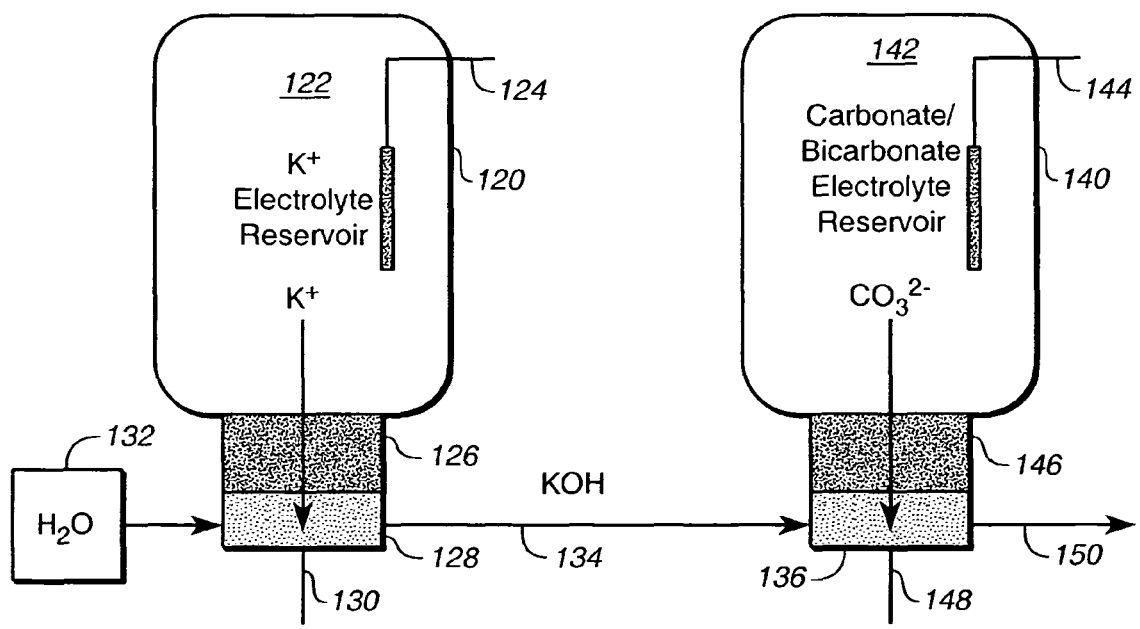
FIG._5

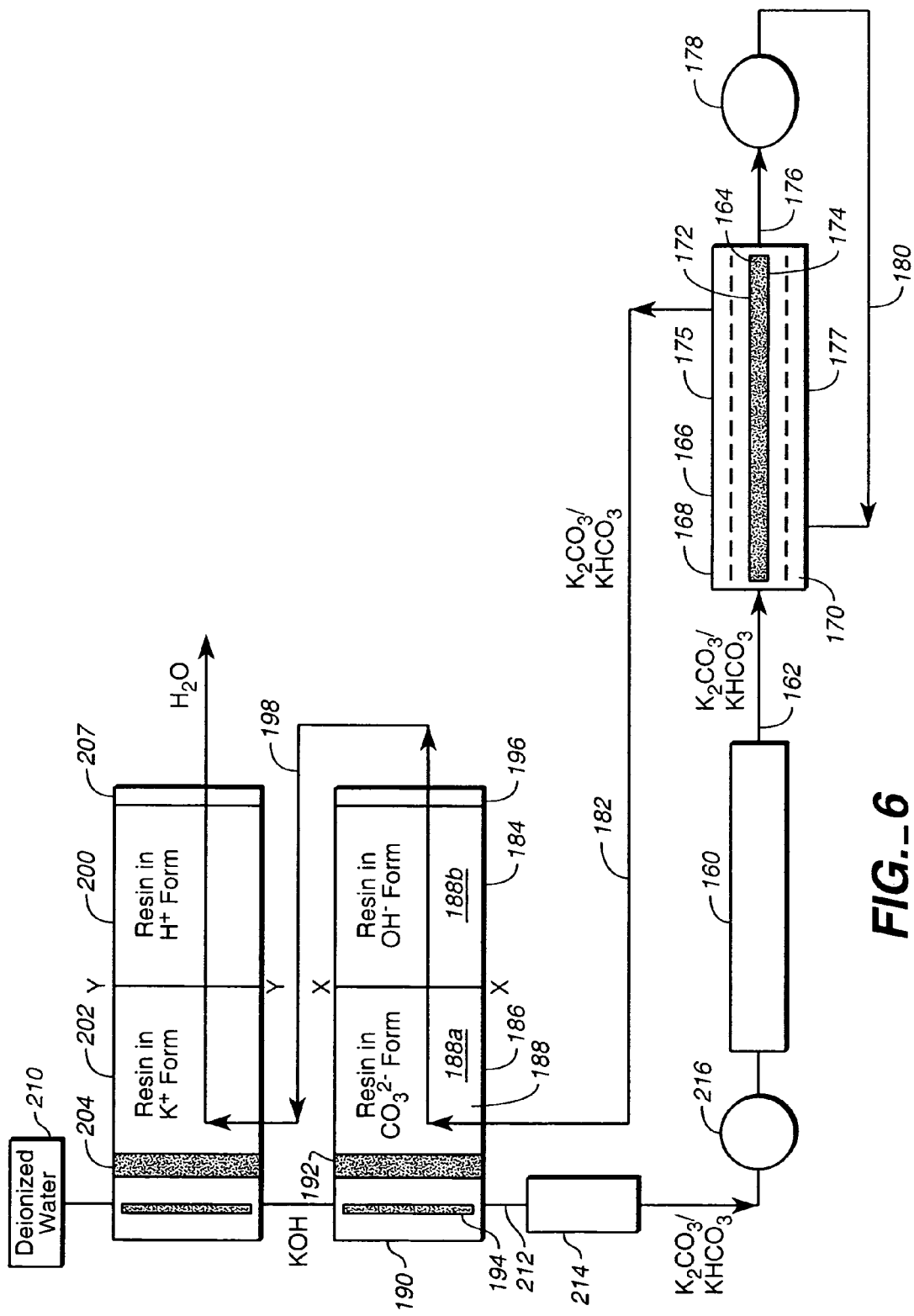
FIG._6

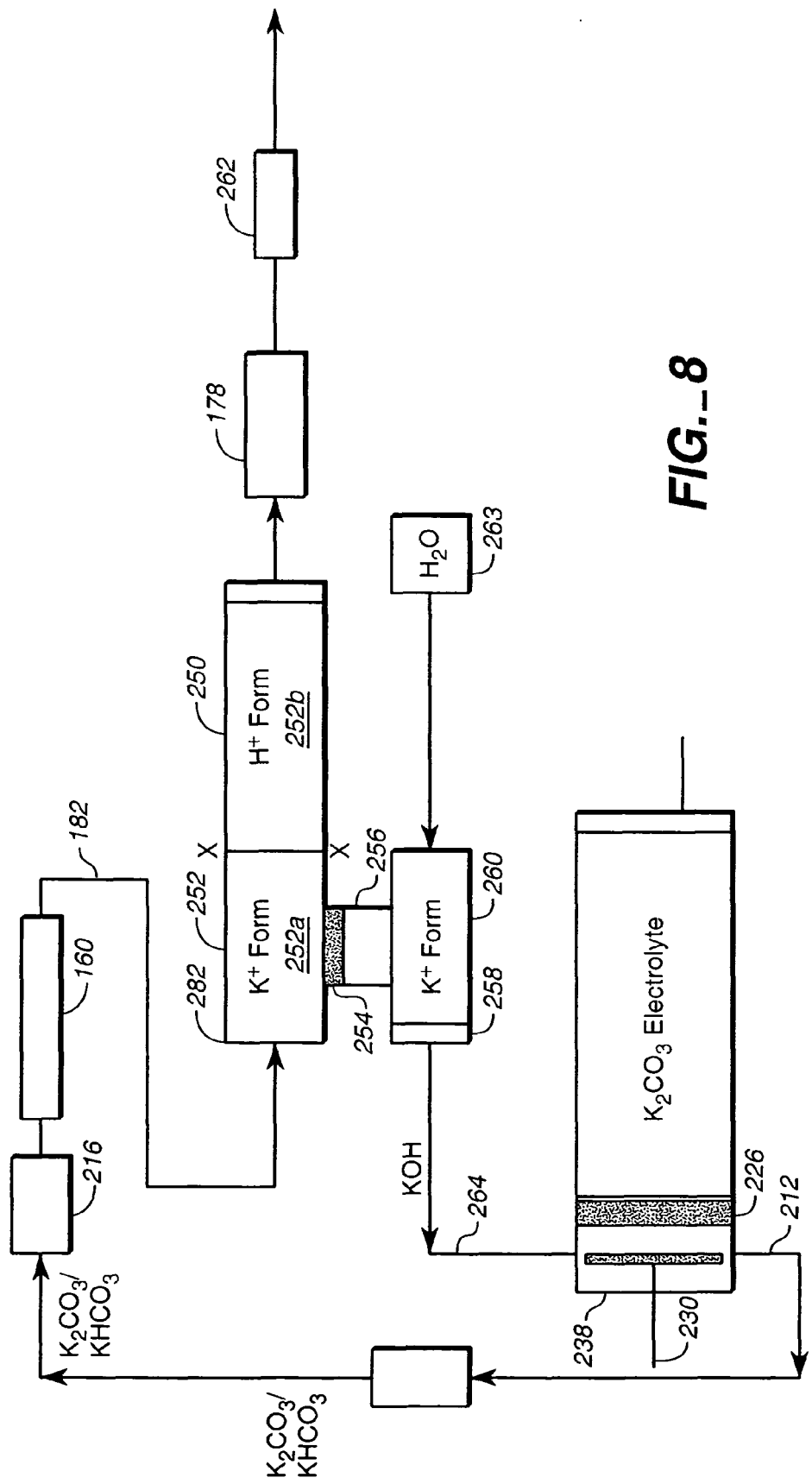
FIG._8

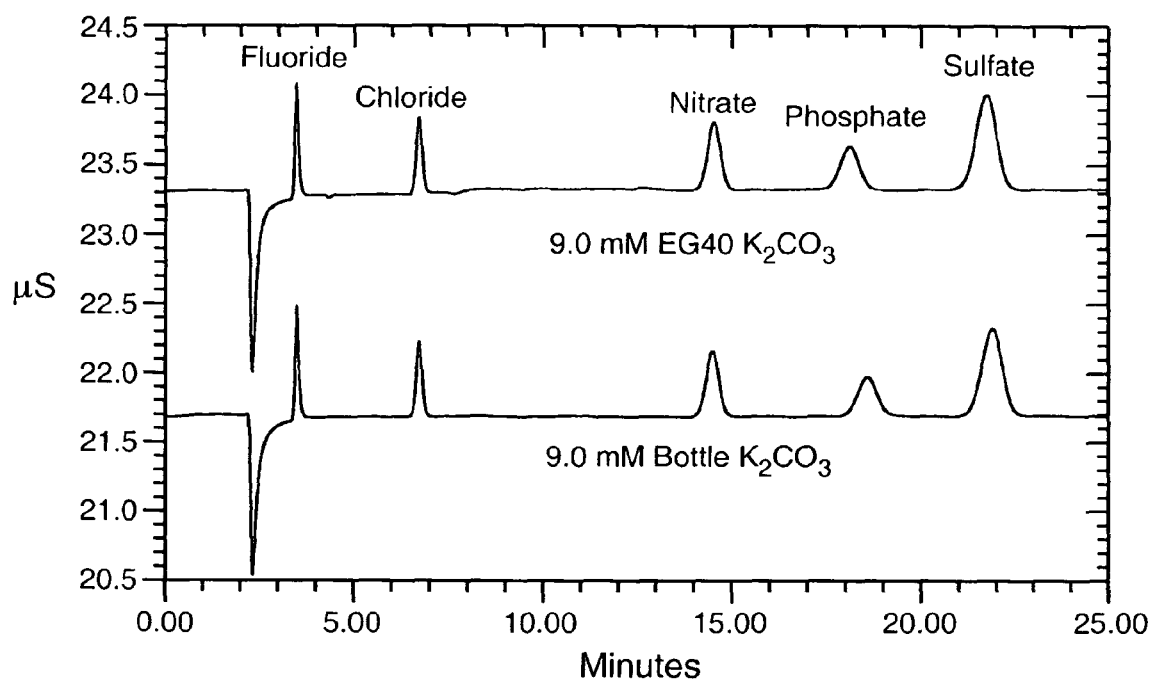
FIG._9
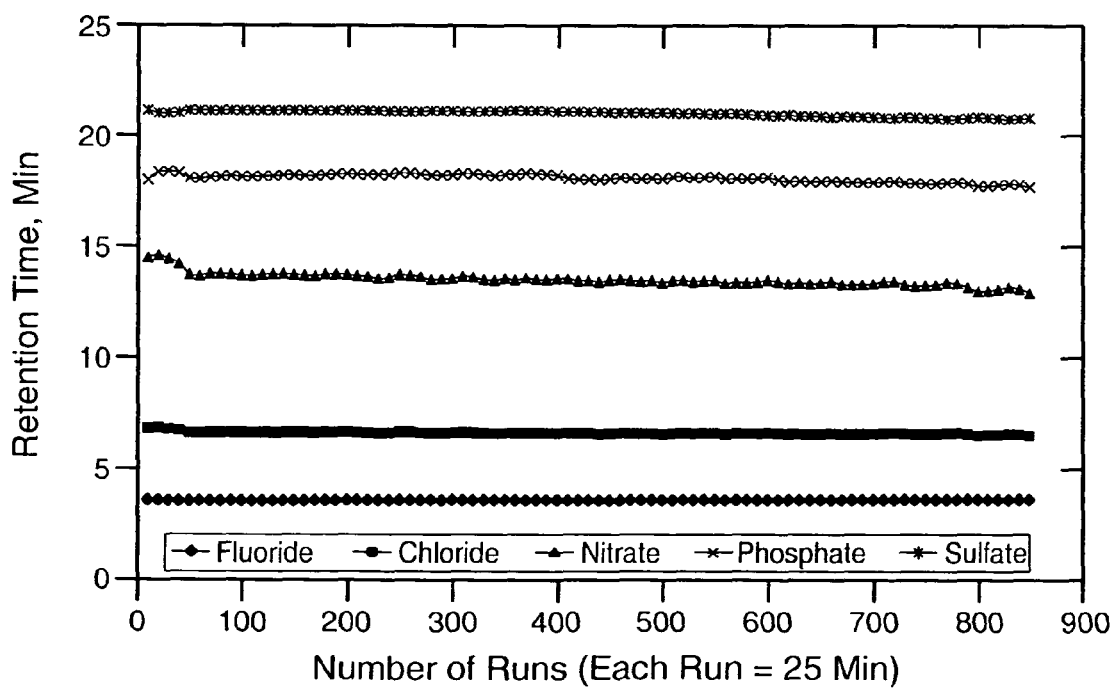
FIG._10

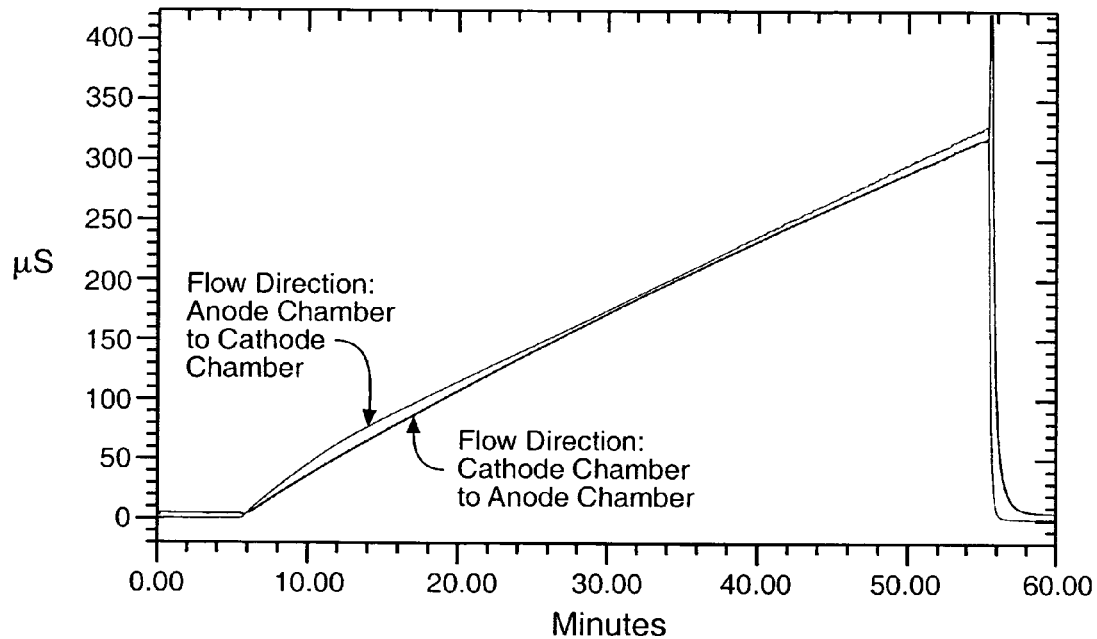
FIG._11
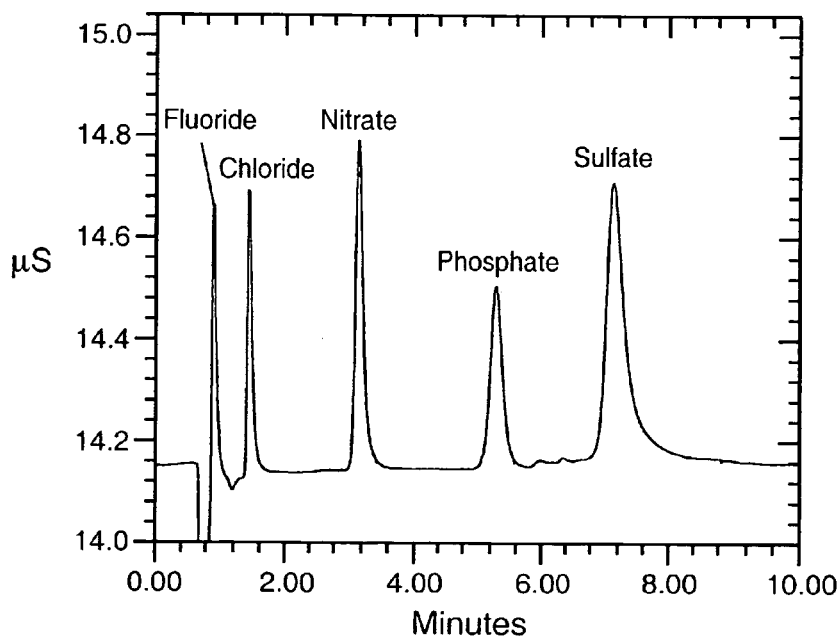
FIG._12

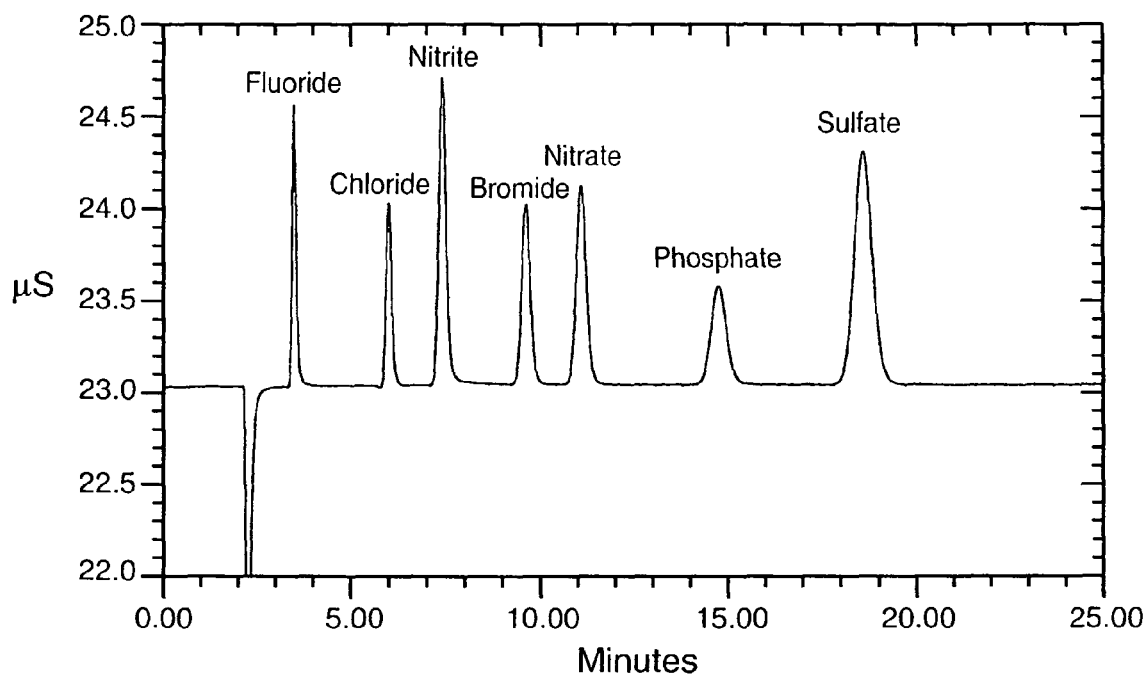
FIG._13
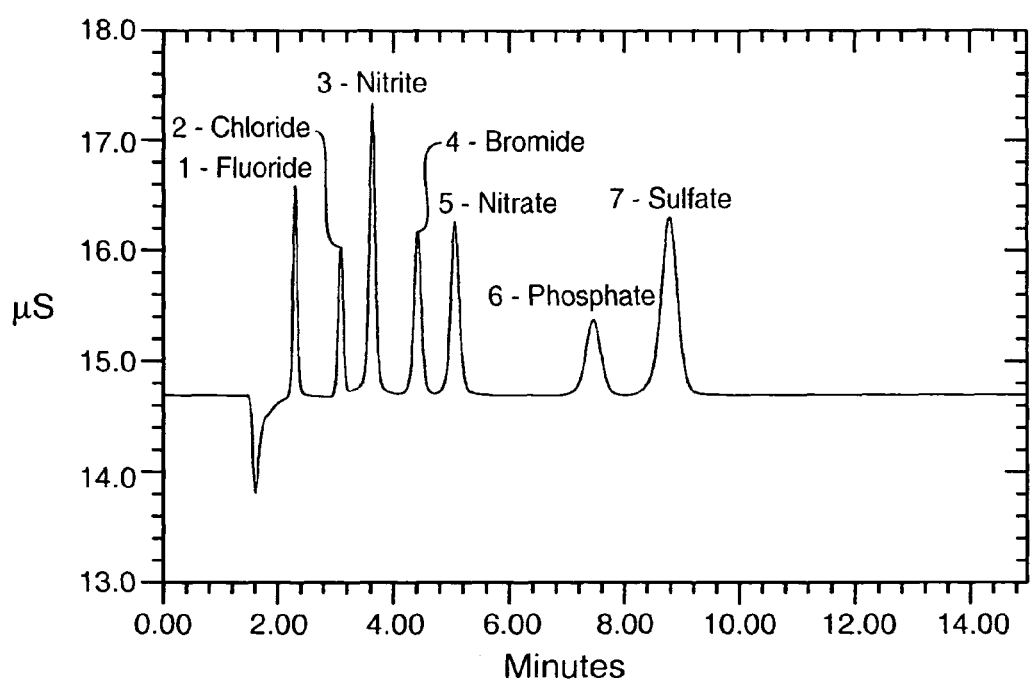
FIG._14

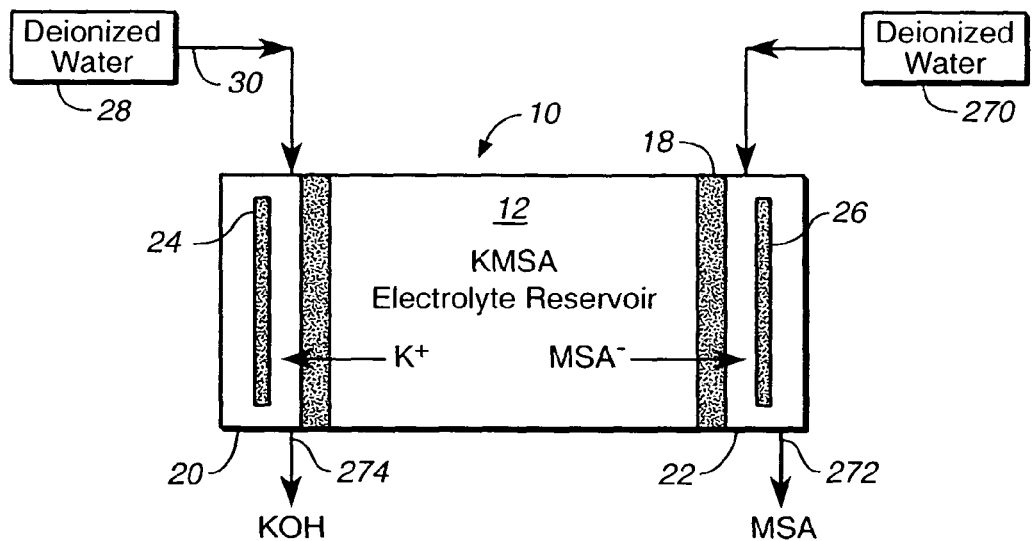
FIG._15
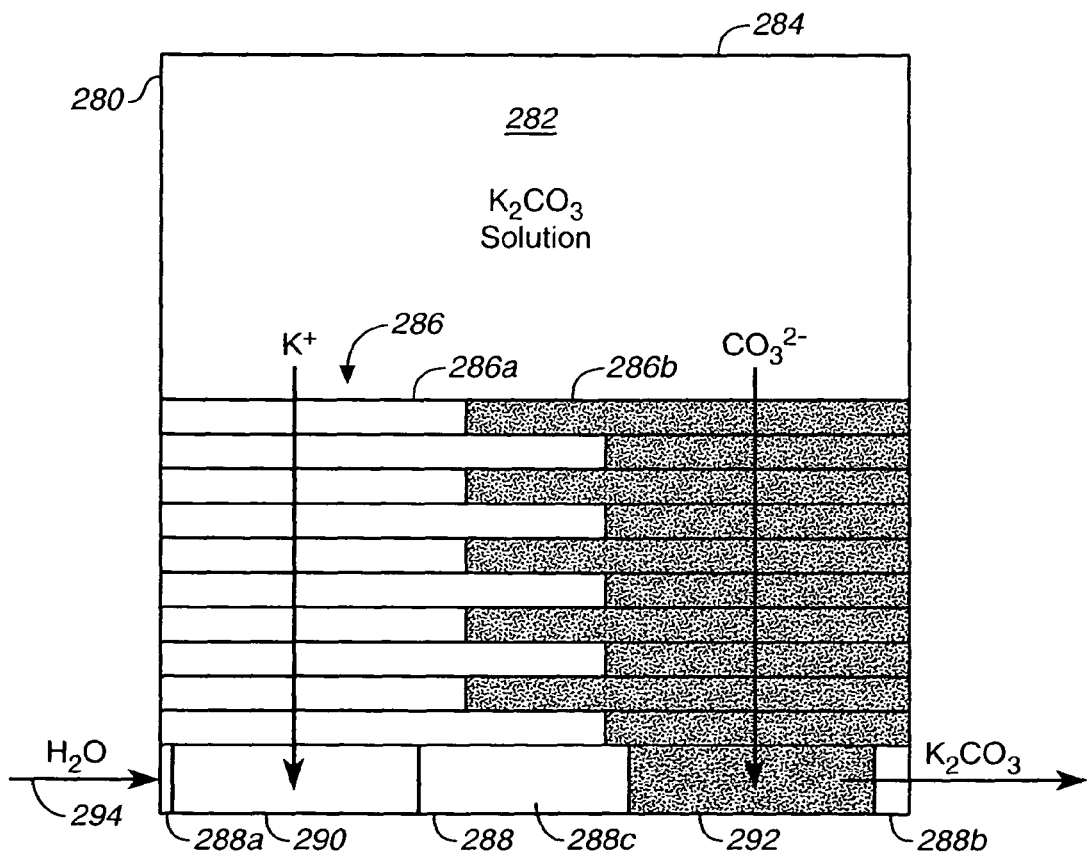
FIG._16

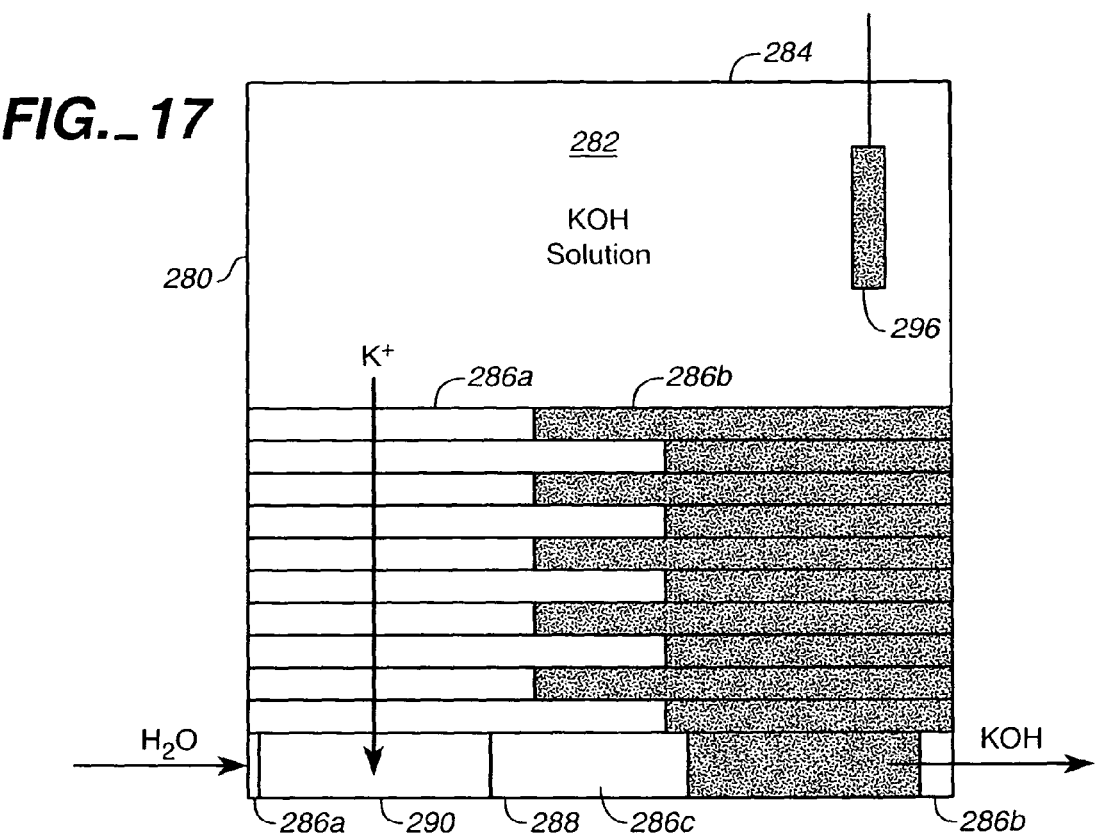
FIG._17
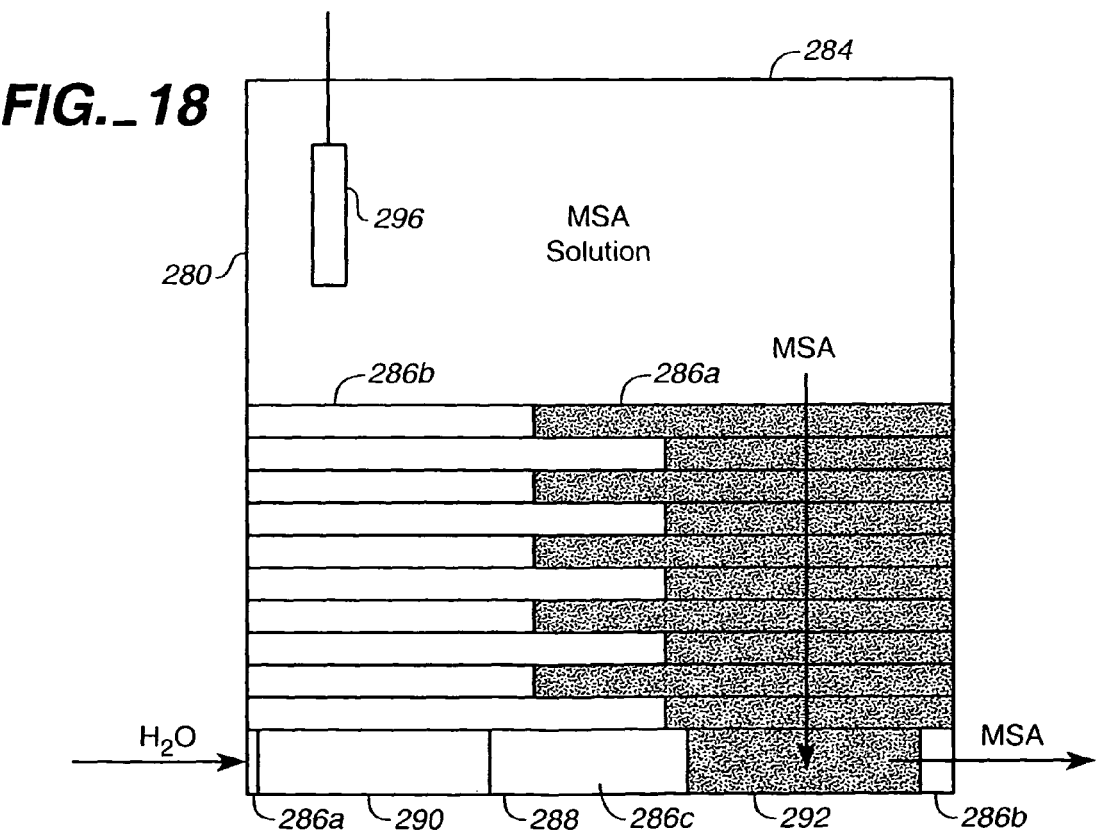
FIG._18

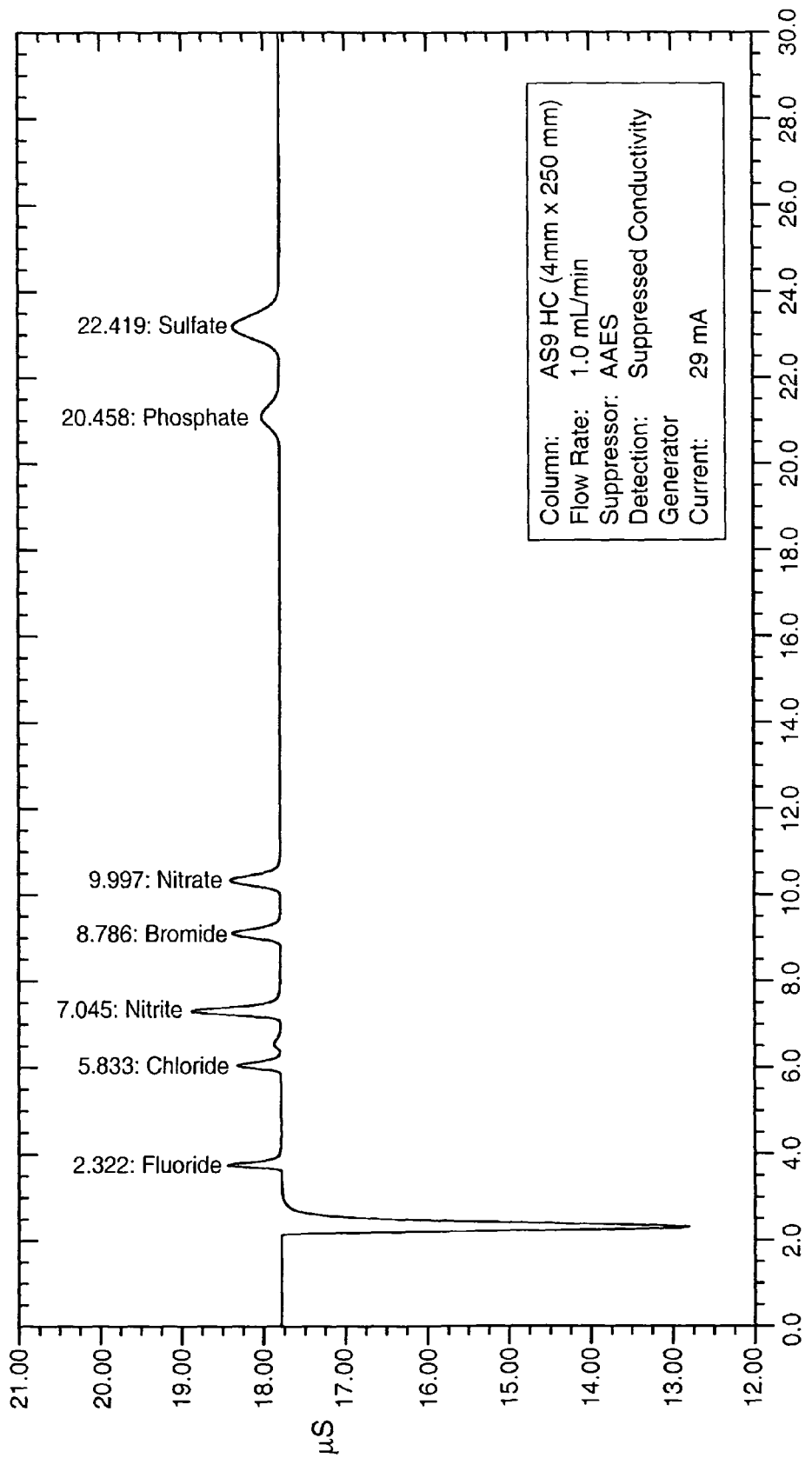
FIG._19

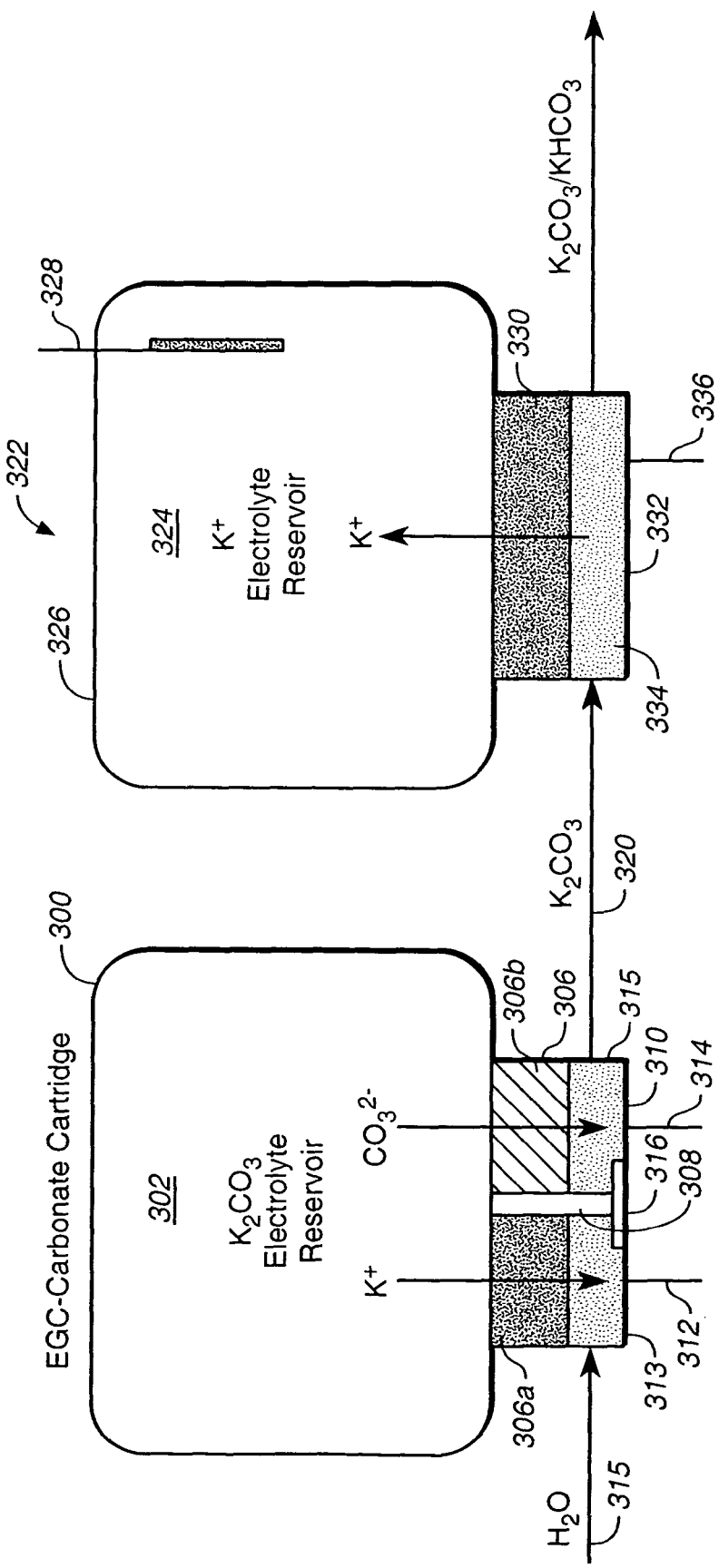
FIG._20

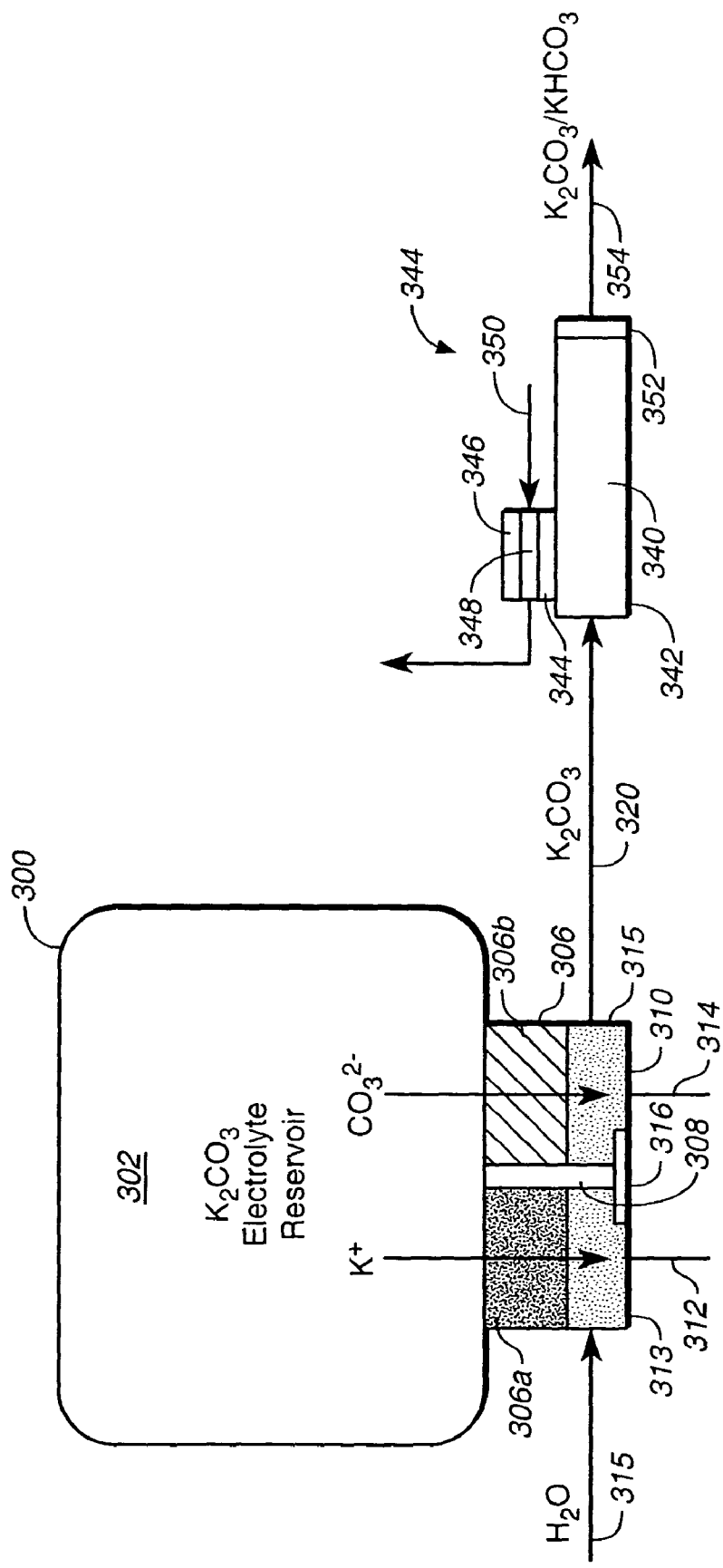
FIG._21

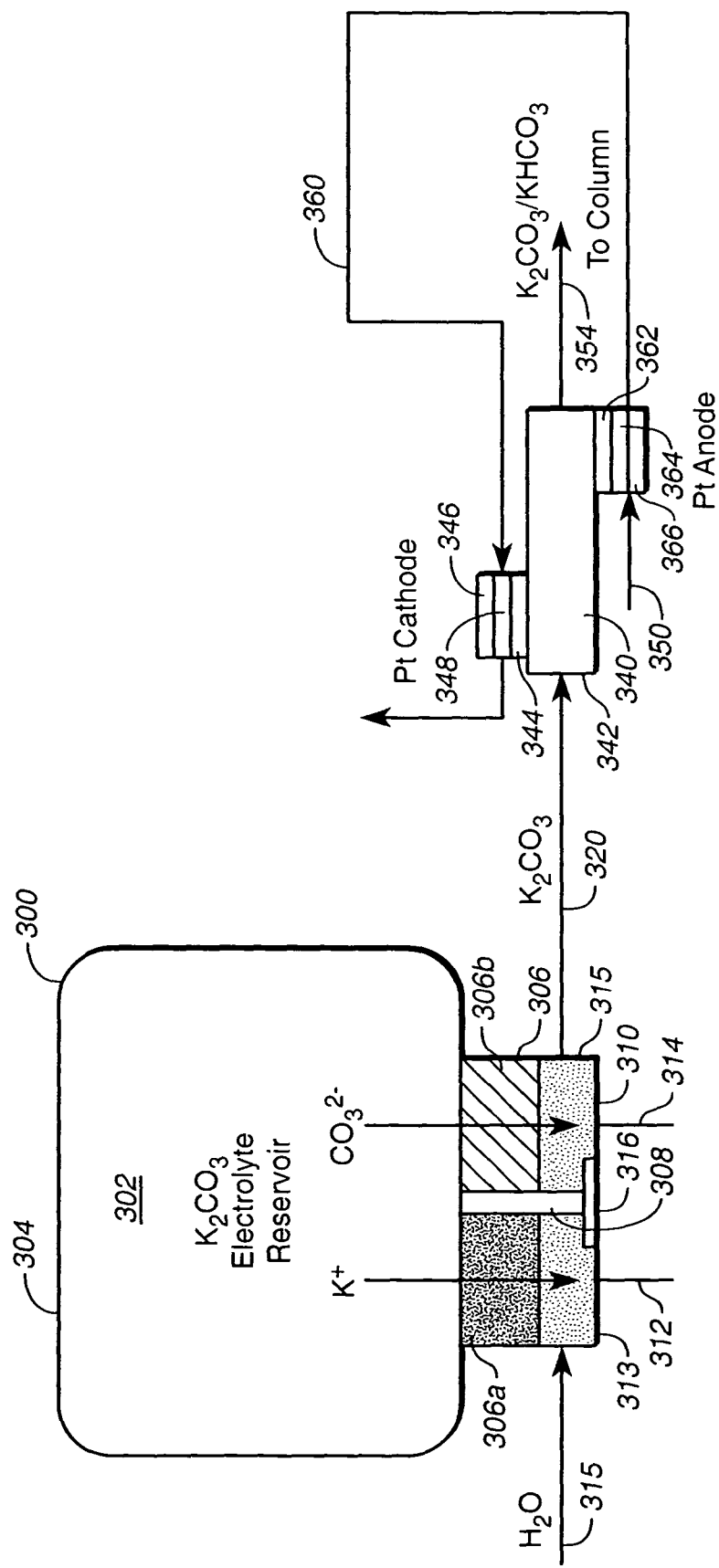
FIG._22

ELECTROLYTIC ELUENT GENERATOR AND METHOD OF USE

CROSS-REFERENCE TO RELATED APPLICATION

This application is a divisional application of U.S. patent application Ser. No. 10/241,361 filed Sep. 11, 2002

BACKGROUND OF THE INVENTION

Ion chromatography and other forms of liquid chromatography are widely used analytical techniques for determination of ionic analytes. Dilute solutions of acids, bases, and salts such as sodium carbonate and sodium bicarbonate are used as eluents in the ion chromatographic separations. Traditionally, these eluents are prepared off-line by dilution with reagent-grade chemicals. Off-line preparation of chromatographic eluents can be tedious and prone to operator errors, and often introduces contaminants. For example, dilute NaOH solutions, widely used as eluents in the ion chromatographic separation of anions, are easily contaminated by carbonate. The preparation of carbonate-free NaOH eluents is difficult because carbonate can be introduced as an impurity from the reagents or by adsorption of carbon dioxide from air. The presence of carbonate in NaOH eluents often compromises the performance of an ion chromatographic method, and can cause an undesirable chromatographic baseline drift during the hydroxide gradient and even irreproducible retention times of target analytes. Therefore, there is a general need for convenient sources of high purity acid, base, or salt for use as eluents in the ion chromatographic separations.

U.S. Pat. No. 5,045,204 describes an impure acid or base is purified in an eluent generator while flowing through a source channel along a permselective ion exchange membrane which separates the source channel from a product channel. The membrane allows selective passage of cations or anions. An electrical potential is applied between the source channel and the product channel so that the anions or cations of the acid or base pass from the former to the latter to generate therein a base or acid with electrolytically generated hydroxide ions or hydronium ions, respectively. This system requires an aqueous stream of acid or base as a starting source or reservoir.

U.S. Pat. Nos. 6,036,921 and 6,225,129 describe electrolytic devices that can be used to generate high purity acid and base solutions by using water as the carrier. Using these devices, high purity, contaminant-free acid or base solutions are automatically generated on-line for use as eluents in chromatographic separations. These devices simplify gradient separations that can now be performed using electrical current gradients with minimal delay instead of using a conventional mechanical gradient pump.

Dilute solutions of salts such as sodium carbonate and sodium bicarbonate are often used as eluents in ion chromatographic separations. One object of the present invention is to develop methods and devices for generating such high purity salt solutions using water as a carrier.

SUMMARY OF THE INVENTION

In one embodiment of the invention, an acid or base is generated in an aqueous solution by the steps of:
(a) providing a source of first ions adjacent an aqueous liquid in a first acid or base generation zone, said first ion source and first zone being separated by a first barrier substantially preventing liquid flow and transporting ions only of the same charge as said first ions,
(b) providing a source of second ions of opposite charge to said first ions adjacent an aqueous liquid in a second acid or base generation zone, said second ion source and second zone being separated by a second barrier substantially preventing liquid flow and transporting ions only of the same charge as said second ions, and
(c) transporting ions of a first charge, positive or negative, across said first barrier by applying an electrical potential through said first zone to electrically charge the same with a charge opposite to said first charge and applying an electrical potential through said second zone to electrically charge the same with a charge opposite to the charge of said first zone so that hydroxide ions are generated in one of said first or second zones and hydronium ions are generated in the other of said first and second zones and ions of opposite charge to the electrical charges of said first and second zones, respectively, are transported across said first and second barriers to combine with said hydroxide or hydronium ions in said first and second zones to generate an acid-containing aqueous solution in one of said first or second zones and a base-containing aqueous solution in the other one.

In another embodiment, an acid or base is generated in an aqueous solution by a method comprising the steps of:
(a) providing a source of first ions adjacent an aqueous liquid in a first zone comprising ion exchange medium having exchangeable ions of the same charge as said first ions, said first ion source and first zone being separated by a first barrier substantially preventing liquid flow and transporting ions only of the same charge as said first ions,
(b) providing a source of second ions of opposite charge to said first ions adjacent an aqueous liquid in a second zone comprising ion exchange medium having exchangeable ions of the same charge as said second ions, said second ion source and second zone being separated by a second barrier substantially preventing liquid flow and transporting ions of only of the same charge as said second ions, said first and second ions being selected from the groups consisting of (1) acid-forming ions or base-forming cations or (2) hydroxide or hydronium ions of opposite charge to (1), so that said first barrier passes ions of groups (1) or (2) but not both and the second barrier passes ions of opposite charge to the first barrier, and
(c) applying an electrical potential through said first zone to electrically charge the same with a charge opposite to that of ions transported across said first barrier and through said second zone to electrically charge the same with a charge opposite to the charge of said first zone so that the ions transported across said first and second barriers into the ion exchange medium in said first and second zones combine therein to generate an acid or a base in the aqueous solutions therein.

In a further embodiment, an apparatus is provided for generating an acid, base or salt-containing aqueous solution comprising:
(a) a source of first ions adjacent an aqueous liquid in a first acid or base generation zone, said first reservoir and first zone being separated by a first barrier portion substantially preventing liquid flow through the first barrier portion and transporting ions only of the same charge as said first ions,
(b) a source of second ions of opposite charge to said first ions adjacent an aqueous liquid in a second acid or base generation zone, said second ion source and second zone being separated by a second barrier portion substantially preventing liquid flow through the second barrier portion and transporting ions only of the same charge as said second ions, and (c) a first electrode in electrical communication with said first zone and a second electrode in electrical communication with said second zone.

BRIEF DESCRIPTION OF THE DRAWINGS

FIGS. 1-8, 15-18 and 20-22 are schematic representations of apparatus according to the present invention.

FIGS. 9-14 and 19 are graphical representations of experimental results using methods according to the present invention.

DETAILED DESCRIPTION OF PREFERRED EMBODIMENTS

Figure 7:
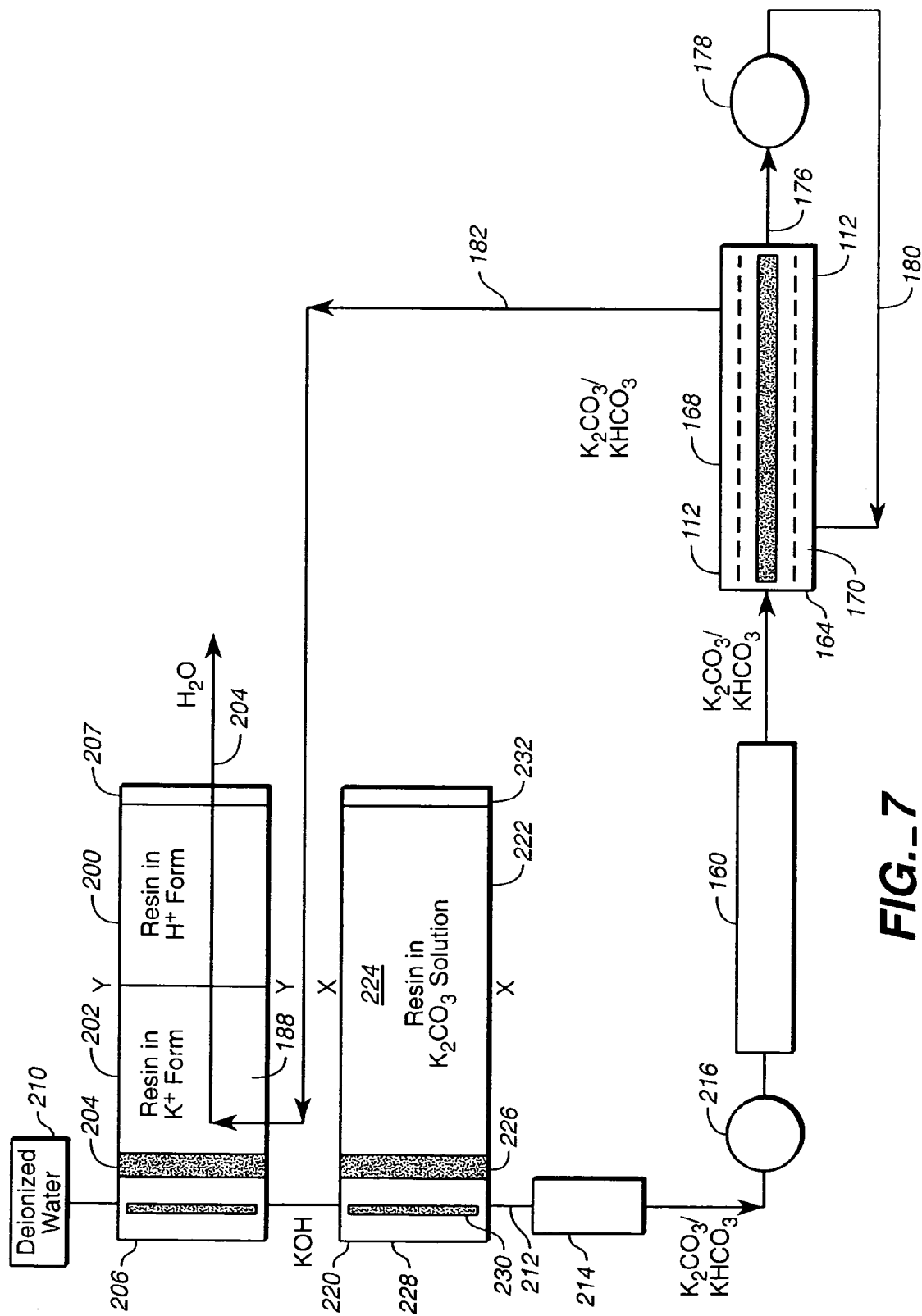

This invention relates to the apparatus and method for generating high purity solutions of salts or acids or bases for use as chromatographic eluents. In ion chromatographic separations with suppressed conductivity detection, dilute solutions of alkali carbonate and bicarbonate (e.g., $K_2CO_3$, $Na_2CO_3$, and $NaHCO_3$) are often used as the eluents. For simplicity, the present invention first will be described with respect to the generation of alkali metal carbonate solutions. The invention also applies to the generation of other salt solutions, acids or bases as described later.

In one embodiment of the present invention, a salt containing aqueous solution, e.g., $K_2CO_3$, is generated according to the following general scheme. An aqueous solution including a source of first ions, e.g., $K^+$ ions, is disposed in the reservoir adjacent to a flowing aqueous liquid in a first acid or base generation chamber. A barrier substantially preventing liquid flow separates the source of first ions while transporting ions only of the same charge as the first ions. An aqueous solution including a source of second ions, e.g., $CO_3^{2-}$, of opposite charge to the first ions also is disposed in the reservoir adjacent to an aqueous liquid solution in a second acid or base generation chamber. The second ion source and the second chamber are separated by a second barrier substantially preventing liquid flow while transporting ions only the same charge as the second ions. An electrical potential is applied between the first chamber and the second chamber across the reservoir so that hydroxide ions are generated in one of the chambers and hydronium ions are generated in the other one. The cations and anions transported across the barriers combine with the hydroxide or hydronium ions, respectively, in the base and acid generator chamber to generate an acid and base. Then, the generated acid and base solutions are mixed in one of the chambers to form a salt containing solution.

Referring to FIG. 1, a block diagram of one form of generator of the foregoing type is illustrated. It will be described with respect to the generation of a pure $K_2CO_3$ aqueous solution from a source of that salt in an electrolyte reservoir within the generator. In this instance, the source of both ions is contained in a single reservoir. Referring to the drawing, the salt generator is contained within a housing 10 in which an aqueous solution of the salt 12 is maintained in central reservoir 14. Opposite ends of the solution 12 in reservoir 14 are in contact with oppositely charged first and second barriers 16 and 18 which substantially prevent bulk liquid flow but transport ions only of the opposite charge as the barriers. As illustrated in FIG. 1, the barriers are independent of each other. However, as illustrated hereinafter, the first and second barrier may be replaced by a single continuous barrier with segments of opposite charge. Base and acid generation first and second zones, illustrated in first and second chambers 20 and 22, respectively, are separated from chamber 14 by cation and anion exchange barriers 16 and 18, respectively. Electrodes 24 and 26 are disposed in chambers 20 and 22, respectively. A source of an aqueous liquid 28, preferably deionized water, is directed by a pump, not shown, through line 30 into chamber 20 where a solution of KOH is formed and from there in line 32 through chamber 22 and out through line 34 in the form of an aqueous salt eluent solution. In another embodiment illustrated hereinafter, the zones are disposed in one chamber. For simplicity of description, the zones will be described in separate chambers unless otherwise specified.

In the illustrated embodiment, electrode 24 is a cathode and chamber 20 is a cathode chamber, while electrode 26 is an anode and chamber 22 is an anode chamber. Electrodes 24 and 26 are connected to a suitable power supply, not shown, to complete the circuit. The positively charged potassium ions electromigrate through barrier 16 toward cathode 24 forming KOH which is directed in line 32 to anode chamber 22. The anion, carbonate, electromigrates across ion exchange barrier 18 toward anode 22 in which carbonic acid is formed by electrolysis. The base in line 32 is mixed in chamber 22 with the formed acid, in turn to form the $K_2CO_3$ eluent.

The form of the anode and cathode chambers, the anodes and cathodes, and the barriers reservoir and chamber sizes, concentrations and volumes of reagents, together with the conditions for electrolytic generation of the $H_2CO_3$ and KOH in the chambers are as generally described in U.S. Pat. No. 6,225,129. Also, as described in that application, control of concentration of the salt may be accomplished by a feedback loop.

The salt (e.g., $K_2CO_3$) solution 12 may be at a suitable concentration to provide the corresponding desired maximum concentration of ions transporting across barriers 16 and 18, respectively. The concentration may be controlled by varying the current as applied to the electrodes. As illustrated, the salt solution 12 is in direct contact with both barriers 16 and 18. A suitable concentration is on the order of 1 to 5 M $K_2CO_3$ with a volume sufficient to provide a reservoir of the $K^+$ ions and $CO_3^{2-}$ ions for generating the salt over an extended period of time (e.g., at least about 100 hours).

In one mode of operation of the apparatus of FIG. 1, the $K_2CO_3$ eluent generator, deionized water is pumped into the cathode chamber, and a DC current is applied to the device. Under the applied electrical field, $K^+$ ions migrate from the electrolyte chamber into the cathode chamber and combine with hydroxide ions produced through the reduction of water at the cathode to form a KOH solution. The KOH solution along with hydrogen gas (an electrolysis product) then flows through the anode chamber where KOH combines with $H_2CO_3$ formed in the anode chamber (and another electrolysis product, oxygen gas) to produce a $K_2CO_3$ solution. The $K_2CO_3$ solution and the electrolysis gases (i.e., hydrogen and oxygen gases) are then passed through a degas tubing assembly (not shown) wherein the electrolysis gases are removed. The $K_2CO_3$ solution is ready to be used as an eluent in an ion chromatography system as illustrated in FIG. 2. The concentration of $K_2CO_3$ generated is directly proportional to the applied current and inversely proportional to the flow rate of deionized water. In addition to the use of deionized water as the carrier, solutions of other reagents such as KOH may be used as the carriers for the device. A mixture of such aqueous solutions and electrolytically-inactive organic solvents may also be used as the carrier.

While not specifically disclosed, an ion exchange resin bed or equivalent may be disposed in chamber 14 in the form of a mixed resin bed (e.g., comprising a cation exchange resin with exchangeable $K^+$ ions and an anion exchange resin with exchangeable carbonate ions) for the purpose of supplying cations and anions to the eluent generator.

The nature of the cations and anions used as the source solution 12 may be of the type described in the last named patent. Thus, suitable cations include metal ions such as alkali and alkaline earth metal ions and suitable anions include organic or inorganic anions such as methanesulfonic acid (MSA), carbonate and sulfate.

Referring to FIG. 2, an ion chromatography system is illustrated utilizing a salt generating cartridge of a similar type to that of FIG. 1. In this instance, the deionized water flows through the anode chamber and the eluent salt solution is formed in the effluent from the cathode chamber, the reverse order of the flow system of FIG. 1.

Referring specifically to FIG. 2, housing 36 contains a source of anions and cations in a salt solution 40 in reservoir chamber 42 in contact at opposite sides with a cation exchange barrier 44 and an anion exchange barrier 46, respectively. To the outside of the barriers are cathode chamber 48 and anode chamber 50 in which are disposed cathode 52 and anode 54 connected to a power source, not shown. An aqueous liquid source in the form of reservoir 56 flows through line 58 and through anode chamber 50 in which acid is formed by electrolysis. From there, the acid flows through line 60 to cathode chamber 48 in which a base is formed by electrolysis. The base mixes with the acid from line 60 to form the electrolyte salt solution which exits in line 62. Electrolysis gases (i.e., hydrogen and oxygen gases) can be passed through a degas tubing assembly 64 of the type described in the aforementioned patent application wherein the electrolysis gases are substantially removed. The $K_2CO_3$ salt solution can then be used in a chromatography system, such as an ion chromatography system as illustrated in FIG. 2. In this instance, the $K_2CO_3$ eluent solution flows in line 66 past a sample injector 68 and through anion separation column 70, suitably a chromatography column of the type described in the aforementioned U.S. Pat. No. 6,225,129. The effluent from the chromatography column can be detected directly or, as illustrated, flow in line 72 through membrane suppressor 74 and through line 76 to a detector 78, suitably a conductivity detector. In the illustrated embodiment, the suppressor may be of the type sold by Dionex Corporation under the trademark SRS7 in which the effluent from the conductivity detector flows in line 80 to be recycled as a source of regenerant solution to the suppressor. The form of suppressor is described in U.S. Pat. No. 5,352,360.

In another embodiment of the invention illustrated in FIG. 3, independent reservoirs of anions and cations are used to form acids and bases, respectively, for mixing into the salt eluent of the present invention. As illustrated, a source of anion is disposed in a cathode reservoir 90 in the form of a $K_2CO_3$ salt solution 92 which is in contact with a barrier 94 which passes anions but not cations and which blocks bulk liquid flow, similar to barrier 16 in FIG. 1. An ion exchange resin bed 96 is disposed in acid generation chamber 98 separated by barrier 94 from the solution in reservoir 90.

Similarly, reservoir 100 contain solution 102 of a cation source which may also be in the form of $K_2CO_3$ salt solution separated by barrier 104 from cation exchange resin bed 106 in base generation chamber 108 disposed adjacent to acid generation chamber 98 at interface 110, in ionic contact, typically in direct physical contact. The structure and electrolytic reactions which take place in the acid generation and base generation sides of the system are similar to those set forth above with respect to FIG. 1. In the illustrated embodiment, cathode 112 is disposed in electrical communication with the solution 92 in reservoir 90 while anode 114 is disposed in electrical communication with the anion source solution 100 in reservoir 102. As illustrated, cathode 112 and anode 114 are disposed in direct contact with the reservoirs solutions and connected to a power source, not shown. Anions (carbonate ions) in reservoir 90 migrate across barrier 94 into generation chamber 98 toward anode 114. Similarly, cations ($K^+$ ions) in reservoir 100 pass through barrier 104 into chamber 106 toward cathode 112. $K^+$ ions combined with $CO_3^{2-}$ ions at interface 110 to form a $K_2CO_3$ salt solution in the $K_2CO_3$ generation column. As illustrated, water from source 116 flows through interface 110 to carry out the $K_2CO_3$ salt solution in stream 112. Similar sizes of the two reservoirs and concentrations of solution and operating conditions as described in U.S. Pat. No. 6,225,129 can be used in this two reservoir system. The concentration of KOH in the base generation column is directly proportional to the applied current and inversely proportional to the flow rate. In the generation of $K_2CO_3$ eluent, KOH is not formed in the cation exchange bed which serves to carry $K^+$ ions to interface 110.

In an embodiment, not shown, the charges in the anode and cathode chambers may be reversed together with the exchangeable ion charges on the barriers and ion exchange resin beds. In this instance, the base is formed in the chamber on the left side of FIG. 3 and is carried by the flowing aqueous stream into the acid formed on the downstream chamber of ion exchange resin.

Also, if desired, the ion exchange beds in the acid or base generation chamber may be formed using ion exchange resins or other materials such as described in U.S. Pat. No. 6,225,129.

In another embodiment not shown, the solutions in the cathode and anode reservoirs may be acids or bases rather than salts so long as the ion which passes through the barriers is present in the respective ion source solutions. Thus, for example, the solution in the cathode reservoir may comprise $H_2CO_3$ and the solution in the anode chamber may comprise a KOH.

Referring to FIG. 4, another embodiment of the invention similar to that of FIG. 3 is illustrated with the exception that the ion exchange beds in the acid and base generation chamber contact each other at an interface which is substantially parallel to rather than transverse to the flow of water from source 116. Like parts in FIGS. 3 and 4 are designated with like numbers. One advantage of this system is that there is increased contact between the cation exchange resin bed and the anion exchange resin bed which can lead to lower device resistance.

In the embodiments of FIGS. 3 and 4, both the cathode and anodes are placed outside of the acid or base generation stream and, thus, the salt generation stream. Because of this placement, the salt solution is free of electrolysis gases. Thus, the use of a somewhat costly degas tube assembly described in FIG. 2 for removing electrolysis gases may be avoided.

Another advantage of the embodiments of FIGS. 3 and 4 is that the same devices used to generate a salt as described above may be used to generate an acid or base eluent by choosing the appropriate electrolyte solution. By way of example of the foregoing principle, the system of FIG. 4 may be used as a large capacity base generator by using a source of potassium in the anode chamber as described above in the form of, for example, potassium hydroxide or potassium salt. However, in the cathode chamber, instead of using a salt or an acid of an ion which passes through the barrier, the same base solution may be used in the cathode and anode reservoirs. For example, 4.0 M KOH solution may be used in both reservoirs. In this manner, the cation in the anode reservoir passes through the barrier into the cation exchange resin while hydroxide electrolytically generated from water in the cathode chamber passes to the anion exchange resin bed in the base generation chamber. $K^+$ ions combine with hydroxide ions at the interface of the cation exchange bed and anion exchange bed to form a KOH solution in the carrier stream. The concentration of the KOH generated is directly proportional to the applied current and inversely proportional to the flow rate.

In another embodiment using the general configuration of FIG. 4, the system may be used as a large capacity acid generator. For example, it could be used to generate methanesulfonic acid (MSA) as the electrolyte solution. In the acid generator embodiment, the polarities are reversed so that the first reservoir is a cathode generator and the second reservoir is an anode reservoir. Also, the barrier for the first reservoir is an anion exchange barrier and the first generator includes an anion exchange bed. Similarly, the second reservoir is an anode reservoir separated from cation exchange bed in the second generation chamber by a cation exchange barrier. The ionized water is pumped into the MSA generation chamber and a DC current is applied between the anode and cathode. Under the applied field, $H^+$ ions in the anode reservoir migrate across the cation exchange barrier into the cation exchange bed, and $MSA^-$ ions in the cathode reservoir migrate across the anion exchange barrier into the anion exchange bed. $H^+$ ions combine with $MSA^-$ ions at the interface of the cation exchange bed and the anion exchange bed to form the acid, MSA solution. The concentration of MSA generated is directly proportional to the applied current and inversely proportional to the flow rate.

FIG. 5 illustrates a dual-reservoir variation of the large capacity salt generator of FIG. 3 is illustrated. Like parts will be designated with like numbers. In this embodiment, electrodes are disposed in or adjacent to the acid and base generation chambers which are isolated from each other. Thus, the electrical circuit is between the electrode in the reservoirs and the oppositely charged electrodes in the acid and base generation chambers, respectively. The two generators can operate in the same general manner as the acid and base generators of the aforementioned patent application in which the acid or base generated in the first acid or base generation chamber is directed in a line to the second acid or base generation chamber to form a salt.

Referring specifically to FIG. 5, first electrolyte reservoir 120 contains a source of cation, e.g., $K^+$ ion, in a solution 122 in the form of a base, e.g., KOH, or a potassium salt. An anode 124 is disposed in reservoir 120 in contact with solution 122 which is also in contact with barrier 126 in the cation exchange form which transports cations but not anions to base generation chamber 128. A cathode 130 is disposed in or in electrical communication with base generation chamber 128. The cations migrate across barrier 126 to electrolytically form a base in base generation chamber 128. The base is carried by water from source 132 through line 134 to the acid generation chamber 136 described hereinafter. The configuration and principles and parameters of operation of the base generation chamber are the same as those disclosed in U.S. Pat. No. 6,225,129.

A second electrolyte reservoir 140 contains a solution of anions which are used to form a salt with the base flowing in line 134 to chamber 136. A cathode 144 is disposed in the solution 142 of anions. To form a common eluent salt for chromatography, the anions may be a mixture of $HCO_3^-/CO_3^{2-}$. In a manner analogous to the cation source reservoirs, these anions may be in a salt form or acid form. The bottom of reservoir 140 is in open communication with anion exchange barrier 146 which is in fluid communication with acid generation chamber 136 in which anode 148 is disposed.

The salt solution formed in chamber 136 flows out line 150 for use as an eluent. The principles of operation of this acid generation section are analogous to the acid generation system described in the last named U.S. patent.

If desired, both electrolyte reservoirs may be filled with a salt, e.g., $K_2CO_3$, as the electrolyte solution. In operation, the ionized water is pumped into the base generation chamber 128 in which KOH solution is electrolytically generated. This base then passes through the acid generation chamber in which $H_2CO_3$ is generated. The acid and base are generated electrolytically and mixed to form $K_2CO_3$ eluent. The devices use two DC power supplies to control the current applied to the acid and base generators 128 and 136, respectively. Since the power supplies are independent, the system is capable of generating different concentrations of KOH and $H_2CO_3$, and thus the system is capable of generating a combination of carbonate and bicarbonate at different concentrations in the eluent. A degas tubing assembly may be placed after the chamber 136 to remove generated electrolysis gases (hydrogen and oxygen).

Referring to FIG. 6, another embodiment of the invention is illustrated using certain principles of a non-integrated ion reflux device for generating an eluent as disclosed in U.S. patent application Ser. No. 09/612,113, filed Jul. 7, 2000. In essence, the system includes in series an acid and a base generation device of the type disclosed in the last named patent application in series to combine the acid and base generated to form a salt which is used as the eluent for chromatography.

One embodiment of the invention is illustrated using an eluent generator of the type described with respect to FIG. 3 of Ser. No. 09/612,113 in combination with a suppressor of the self-regenerating type described in U.S. Pat. No. 5,248, 426. Referring to FIG. 3 of that application, a membrane suppressor is illustrated in which effluent from chromatography separator 160 in the form of an anion resin bed separation column passes through the chromatography effluent compartment 164 of sandwich membrane suppressor 166. In this instance, the chromatography effluent compartment is sandwiched between two detector effluent compartments 168 and 170 separated therefrom by cation exchange membranes 172 and 174, respectively. The structure of the membrane suppressor, which may be of the type disclosed in U.S. Pat. No. 5,352,360, may include ion conducting materials, not shown, placed in any of the compartments 164, 168 or 170 to improve the current efficiency of the device. An electrical potential is applied across the flow path through sandwich suppressor 166, suitably by flat plate electrodes 175 and 177 disposed at the outside of the detector effluent compartments as described in the above patent.

The suppressor effluent flows through line 176 to conductivity cell 178 for recycle in line 180 back to detector effluent compartments 168 and 170 serving as the flowing aqueous stream for the generation of a salt for the suppression of the eluent in the chromatography effluent flowing into the suppressor in line 162. Details of operation of this type of recycle suppressor to accomplish these objectives is described in U.S. Pat. No. 5,350,360. The effluent from suppressor 116 containing a salt flows through line 182 to an acid generator and eventually to a base generator, both of the types described in U.S. patent application Ser. No. 09/612,174. Conduit 182 is provided to direct the salt stream from suppressor 166 to the inlet of eluent generator 184. This system operates substantially the same as the base generator described with respect to FIG. 3 of the last named patent application. It includes a suitable housing 186 containing an electrolyte ion reservoir in the form of a packed bed of ion exchange resin 188. Resin bed 188 is separated from a first generator electrode chamber 190 by a charged generator barrier 192 which prevents significant liquid flow but permits transport of electrolyte ions, in this instance anions, analogous to the barriers described herein. An acid generation electrode (anode) 194 is disposed in acid generation electrode chamber 190. At the opposite end of barrier 160 from electrode 194 is a flow-through electrode (cathode) 196.

For the analysis of anions, acid is generated in acid generator 184 for mixing with the base generated by a second generator to be described, forming a salt. The line X-X separates the inlet section 188$a$ from the outlet section 188$b$ of resin bed 188. The stream from suppressor 168 in line 182 flows into inlet section 188$a$ in salt form so that the resin is in $CO_3^{2-}$ form while the outlet section is in the hydroxide ion form. The aqueous stream exits acid generator 184 through electrode 196 and exits the resin bed in line 198. The exiting solution in conduit 198 is directed to a base generator 200 with a resin and components of opposite polarity to acid generator 184. There, the resin bed 202 is in the cation (potassium) form to the left of line Y-Y while the bed to the right of line Y-Y is in hydronium ion form. The solution flows through the bed and exits through electrode 207 through line 204 to waste. Resin bed 202 is separated by cation exchange barrier 204 from that base generation chamber 206 containing cathode 208. The deionized water from source 210 flows through chamber 206 to carry the base generated therein to acid generation chamber 190 which they are mixed to form an aqueous salt solution. The salt solution flows through line 212 to a degas tube at 214 of the type described above and from there to a sample injector 216 to serve as the eluent which carries the liquid sample to anion separator column 160. If desired, all of the foregoing polarities may be reversed so that eluent generator 184 generates base and eluent generator 200 generates acid.

In operation, deionized water is pumped into the KOH generation chamber in which the KOH solution is electrolytically generated and then flows to the acid generation chamber in which the base combines with the acid which is electrolytically generated to form a salt (potassium carbonate) eluent. The device uses two DC power supplies to control the currents that are independently applied to the acid and base generation chambers so that combinations of carbonate and bicarbonate at different concentrations may be generated. To avoid ion contamination from samples, a high capacity cation exchange trap column, e.g., in $K^+$ form, and a high capacity anion exchange trap column, e.g., in carbonate form, not shown, can be placed in line 182.

Referring to FIG. 7, another embodiment of the invention based on a non-integrated ion reflux device is illustrated similar to the device of FIG. 6. From the point at which the component ions of the salt eluent generated is recycled from the suppressor effluent, the system of FIG. 6 is the same as that of FIG. 7. Thus, like parts will be designated with like numbers in the above descriptions of such components are incorporated at this point by reference. Like the embodiment of FIG. 6, FIG. 7 illustrates a system in which acid is electrolytically regenerated in an acid generation chamber, the base is generated in a base generation chamber and the regenerated acids and bases are mixed to form the chromatography eluent. In this embodiment, the recycled effluent in line 182 from suppressor 112 only flows through the base generation unit while the acid generation unit operates with an anion source solution in a substantially non-flowing reservoir which can be replenished.

The base generation unit 200 is of the same configuration as corresponding unit 200 of FIG. 6. In this instance, the salt solution in recycle line 162 flows directly into and through the resin bed 200 and out porous anode 207 from left to right as illustrated.

As the device of FIG. 6, the deionized water from source 210 flows through the base generation chamber 206 in which base (e.g., KOH) is electrolytically generated. This generated base is carried in deionized water from source 210 into the acid generation unit 220 which includes a housing 222 and a reservoir 224 of an aqueous solution of an anion source such as a salt (e.g., $K_2CO_3$) or acid (carbonate acid). On one side of reservoir 224 is an anion exchange barrier 226 which selectively passes anions but blocks bulk liquid flow to acid generation chamber 228 in which is disposed anode 230. At the opposite end of reservoir 224, from barrier 226 is a cathode 232. The principle of operation of unit 220 in isolation is the same as that described with respect to FIG. 1 of U.S. Pat. No. 6,225,129. In this instance, reservoir 224 is the anion source that electromigrates across barrier 226 toward anode 230 to form the acid solution.

In operation, the deionized water is pumped from source 210 into the base generation chamber 208 in which a base is electrolytically generated. A KOH solution passes through acid generation chamber 228 in which acid is electrolytically regenerated to form a potassium carbonate salt. The device uses two DC power supplies to control the currents which are independently applied. Thus, the device is capable of generating KOH and $H_2CO_3$ at different concentrations and thus generating combinations of carbonate and bicarbonate at different concentrations in the eluents.

In contrast to the system of FIG. 6, in FIG. 7 only the cations (e.g., potassium ions) are recycled. Such recycle is accomplished by passing the regenerant effluent from the electrolytic suppressor in line 182 through the cation exchange resin bed 200 to the base generation unit. The anions (carbonate ions) are not recycled.

FIG. 8 illustrates another embodiment of the invention in which includes an integrated combination suppressor and acid or base generator of the type described with respect to various embodiments of U.S. Pat. No. 6,027,643. Like parts to those of FIG. 7 will be designated with like numbers. This specific form of combination is illustrated with respect to FIG. 11 of that patent. In this instance, for anion analysis, a base is generated by the combination suppressor/base generator for direction to an acid generator/salt mixing unit of the type illustrated under numeral 220 of FIG. 7.

In operation, the effluent in line 212 flows through degas tubing 214 to the sample injector 216 serving as the eluent to carry the sample through separation column 160 and line 182 to combination suppressor/eluent generator 250. Stream 182 passes through an ion exchange bed 252 including an upstream portion 252$a$ in cation ($K^+$) form adjacent at line X-X to a downstream portion 252$b$ in the hydrogen ion form. An ion exchange barrier 254 is in contact with resin bed 252 and with a resin bridge 256 between barrier 254 and flow-through cathode 258 at the outlet end of cathode chamber 260 in which a base (KOH) is electrolytically generated. The structure and principles of operation of this combination suppressor/eluent generator is described fully in U.S. Pat. No. 6,027,643. As described, the system can also be used for cation analysis in which the resin in the suppressor is in anion form. Also, the other embodiments of the combination suppressor/eluent generator disclosed in that patent may also be employed. Moreover, as disclosed in that patent, a restrictor 262 is preferably used at the outlet of the conductivity detector for reasons disclosed in that patent.

Water from source 263 carries the aqueous base solution formed in cathode chamber 260 flows in line 264 to anode chamber 228 and which acid is electrolytically generated as described above. The acid and base are mixed to form an eluent salt which flows in line 212, also as described above.

As with the embodiment of FIG. 7, the device uses two DC power supplies to control currents that are independently applied to the acid and base generator portions of the system. Thus, this system is capable of generating any combination of carbonate and bicarbonate at different concentrations in the eluent.

Referring to FIG. 15, another embodiment of the invention is illustrated using electrolytic device similar to that of FIG. 1 for simultaneous generation of base and acid solutions. Like parts will be designated with like numbers. One difference between the two devices is that there is no conduit connecting the output from cathode chamber 24 and the anode chamber 22. Instead, deionized water flows through anode chamber 26 to generate an acid solution.

The salt in electrolyte reservoir 12 is potassium methanesulfonate (KMSA) rather than $K_2CO_3$ because methanesulfonic acid (MSA) is a common acid used as an eluent in chromatography. As illustrated, a source of deionized water flows through acid generator chamber 22 and the acid generated in that chamber flows out of the system in line 272, suitable for use as a chromatography eluent. If desired, deionized water from sources 28 and 270 may be supplied from a single source, not shown. The base (KOH) flows out of the system in line 274 and is suitable for use a chromatography eluent for the separation of anions. Overall, the principle of operation of the salt generator of FIG. 1 and the simultaneous acid and base generator of FIG. 15 are the same with the exception that the acid and base is generated independently and not mixed. Thus, referring to FIG. 2, the generated salt would flow through a degassed tubing 64, sample injector 68, anion exchange separation column 70, anion suppressor 74 and conductivity detector 78. Similarly, the base stream in line 274 can flow through a similar system using the KOH as an eluent for anion chromatography. In like manner, MSA in line 272 can flow through an independent ion chromatography system with the exception that the separation column is a cation separation column rather than an anion separation column and the suppressor is a cation suppressor rather than an anion suppressor.

FIG. 16 illustrates a single reservoir salt generator which is similar in principle to the salt generator of FIG. 3. However, it requires only a single electrolyte reservoir and high pressure eluent generation chamber and uses an integral barrier containing adjacent anionic and cationic functionality which may be in the form of adjacent stacks of ion exchange membranes of opposite polarity. As illustrated, the high pressure eluent generation chamber contains both the anode and the cathode.

Referring specifically to FIG. 16, a block diagram of one form of generator of this type is illustrated. It will be described with respect to the generation of a $K_2CO_3$ aqueous solution from a source of that salt in an electrolytic reservoir within the generator. The generator is contained within a housing 280 in which an aqueous solution of the salt 282 is maintained in reservoir 284. One end of the solution reservoir 284 is in contact with a continuous charged barrier 286 which substantially prevents bulk liquid flow but which transports ions only of the opposite charge as the charged barrier portions adjacent to the solution 282 and reservoir 284. As illustrated, barrier 286 includes two barrier portions 286a and 286b which in composite form a continuous barrier against liquid flow. Barrier portion 286a has exchangeable ions of positive charge which permit the passage of $K^+$ ions but which blocks the passage of $CO_3^{-2}$. Barrier portion 286a is in contact with and integral with barrier portion 286b which passes negative ions such as $CO_3^{-2}$ but which blocks the flow of $K^+$ ions. In composite, barrier portions 286a and 286b block the flow of block bulk liquid flow from reservoir 284 through barrier 286.

As illustrated, barrier 286 is formed of a series of stacked membranes which interleave with each other so that the positively charged membrane 286a extend between pairs of negatively charged membranes 286b. The overlap assists sealing at high pressures against liquid leaks. Alternatively, other forms of positive and positively charged and negatively charged barrier portions without interleaving may be used so long as there is a continuous path for the corresponding ions in solution 282 through the membranes and bulk liquid flow is blocked. For example, an inert plastic spacer may be used to separate the different charged barriers.

As illustrated, a high pressure eluent generator 288 is disposed on the opposite side of barrier 286 from reservoir 284. Adjacent barrier portion 286a is cathode 290 while adjacent barrier portion 286b is anode 292. The cathode and anodes may be of the type described above. A continuous fluid path is provided from inlet end 288a to outlet end 288b of eluent generation chamber 288. An open space 288c may be provided separating cathode 290 and anode 292. Deionized water from a source 294 flows through eluent generation chamber 288. A DC electrical current is applied to the anode and cathode. Under the applied electric field, potassium ions in the electrolyte reservoir 284 migrate across the stack of cation exchange membranes of barrier portion 296a and combine with the hydroxide ions formed at the cathode by the reduction of water to form a KOH solution.

Simultaneously, carbonate ions migrate across the stack of anion exchange membranes in the form of barrier portion 286b and combine with hydronium ions formed at anode 292 by the oxidation of water to form a carbonic acid solution. The potassium hydroxide solution reacts with the carbonic acid solution to form a potassium carbonate solution in the region of anode 292 which flows out outlet 288b. The potassium carbonate may be used as an eluent in chromatography, e.g., in ion chromatography, as illustrated in the flow system of FIG. 2. The concentration of potassium carbonate formed is directly proportional to the applied DC current and inversely proportional to the flow rate of deionized water pumped into the eluent generation chamber.

In another embodiment, illustrated in FIG. 17, a structure including features described in the embodiment of FIG. 16 can be used as a large capacity acid or base generator. Like parts will be designated with like numbers for FIGS. 16 and 17. As illustrated in FIG. 17, the solution in reservoir 284 is potassium hydroxide solution. Instead of disposing an anode in the eluent generation chamber, an anode 296 is disposed in reservoir 284. The electrical path is between anode 296 and cathode 290 and $K^+$ ions flow through the stack of positively charged membranes in barrier portion 286a. The device can be operated as a large capacity KOH eluent generator as described in U.S. Pat. No. 6,225,129.

In another embodiment shown in FIG. 18, the basic structure of FIG. 17 may be used for generation of an acid, e.g., methanesulfonic acid (MSA) solution using the same solution as in reservoir 284. In this instance, the anode 292 is included in eluent generation chamber 288 and the cathode is eliminated from the chamber. Instead, the cathode is disposed in contact with the solution reservoir 284. The electrical path is between the cathode and anode through the barrier portion 286b in the form of a stack of anion exchange membranes.

In another embodiment, after forming a salt-containing solution by any of the foregoing methods using any of the foregoing types of apparatus, the solution is directed to an electrolytic pH modifier device in which the pH level of the salt-containing solution is modified. For example, the pH of an alkali metal salt of a weak acid would be raised to form a salt of a conjugate acid anion in a mixture with the weak acid anion. Examples of such modifications include partially converting the weak acid anions in $K_2CO_3$ or $K_3PO_4$ to one of their conjugate acid forms, $H_2CO_3$ or $HCO_3^{-1}$ or $KHPO_4^{-2}$ or $KH_2PO_4^{-1}$. The salt leaving the pH modifier typically includes a mixture of the alkali metal weak acid salt and the alkali metal conjugate acid salt.

Referring to FIG. 20, one embodiment of salt-forming apparatus in combination with an electrolytic pH modifier is illustrated. In this instance, the salt is formed by a dual-ion exchange zone/single reservoir salt-forming generator somewhat modified from such a generator illustrated in FIG. 16. It will be described with respect to the generation of $K_2CO_3$ aqueous solution from a source of that salt in an electrolytic reservoir within the generator. The generator is contained in a reservoir 300 in which an aqueous solution of the salt 302 is maintained. One end of the salt solution 302 is in contact with a salt charged barrier 306 which substantially prevents bulk liquid flow but which transports ions only of the opposite charge as the respectively charged barrier portion adjacent to the solution 302 in reservoir 300. As illustrated, barrier 306 includes two barrier portions 306a and 306b separated by a plastic insulator 308 forming a composite continuous barrier against bulk liquid flow. The barriers may be of the same type described above. As illustrated, barrier portion 306a includes exchangeable cations while barrier portion 306b includes exchangeable anions so that potassium ions migrate through barrier portion 306a and carbonate ions migrate through barrier portion 306b under the applied electric field. The plastic insulator extends across the length of barrier portions 306a and 306b and electrically isolates them from each other. Thus, barrier portion 306a has exchangeable ions of positive charge which permit the passage of $K^+$ ions but which blocks the passage of $CO_3^{-2}$ ions. Likewise, barrier portion 306b passes negative ions such as $CO_3^{-2}$ which blocks the flow of $K^+$ ions.

As illustrated, a high pressure eluent generator 310 is disposed on the opposite side of barrier 306 from reservoir 304. Adjacent barrier portion 306a is a cathode 312 disposed in a cation exchange resin bed 313 while adjacent barrier portion 306b is an anode 314 disposed in an anion exchange resin bed 315. A fluid path is provided through insulator 308 in the form of a cut-out 316 or the like. The ionized water from a source 315 flows through eluent generator chamber 310. A DC electric current is applied to the anode and cathode. Under the applied electric field, potassium ions in the electrolytic reservoir 304 migrate across barrier portion 306a and combine with hydroxide ions forms at the cathode by the reduction of water to form a KOH solution.

Simultaneously, carbonate ions migrate across barrier portion 306b and combine with hydronium ions formed at anode 314 by the oxidation of water to form a carbonic acid solution. The potassium hydroxide solution reacts with the carbonic acid solution to form a potassium carbonate solution in the region of anode 314 which flows out in line 320.

Referring again to FIG. 20, the $K_2CO_3$ flows in line 320 to electrolytic pH modifying device 322 of the general type illustrated in U.S. Pat. No. 6,225,129 which includes an aqueous solution 324 in a reservoir 326. A cathode 328 is disposed in solution 324. A charged barrier 330 is in contact with solution 324 which substantially prevents bulk liquid flow but which transports ions only of the opposite charge as the charged barrier. For the transport of $K^+$ ions as illustrated, barrier 330 includes exchangeable cations. The salt in line 320 flows through pH modifying flow channel 332 which contains flow-through cation resin exchange bed 334 in electrical communication with anode 336. By passing a DC current between cathode 328 and anode 336, a controlled amount of hydronium ions displaces potassium ions in flow channel 332 to convert a controlled amount of $K_2CO_3$ into $KHCO_3$ and thus generates a carbonate/bicarbonate eluent with the desired concentration ratio $K_2CO_3$ to $KHCO_3$. Expressed generically, the carbonate salt is an acid and is partially converted to the bicarbonate (conjugate acid), both in salt form. Other conversions of acid to conjugate acids can be accomplished by the apparatus of the present invention where salts of weak acid such as $K_3PO_4$.

In another embodiment illustrated in FIG. 21, the salt eluent generator is of the same type as illustrated in FIG. 20. In this instance, the pH modifying device 341 may be of the general type illustrated in U.S. Pat. No. 6,325,976 with the exception that the feed solution is $K_2CO_3$ and that the ion exchange resin bed serves the function of pH modification, not suppression. Like parts will be designated with like numbers for FIGS. 20 and 21. As illustrated, the salt solution in line 320 flows through ion exchange resin bed 340 contained within flow-through housing 342. In this embodiment, the ion exchange resin 340 is a cation exchange resin. The electrolytic pH modifier may be of the same general type as illustrated in FIG. 1 of U.S. Pat. No. 6,325,976. Thus, it includes a barrier 344 which separates bed 340 from an electrode 346 in a hollow housing defining electrode chamber 348 preventing bulk liquid flow but permitting transport of ions only of the same charge as the charge of the exchangeable ions in resin bed 340. In the illustrated system, barrier 344 is in the form of a cation exchange membrane or plug and electrode 348 is a cathode. An aqueous solution from a source 350 continuously flows through chamber 346. The salt in line 320 flows through ion exchange bed 340, porous electrode 352 and out line 354 in the form of a $K_2CO_3/KHCO_3$ solution. The principle of transporting potassium ions across membrane 344 and simultaneously converting part of the salt of the weak acid to its bicarbonate form are the same as illustrated with respect to the embodiment of FIG. 20.

Referring to FIG. 22, another embodiment of the invention is illustrated similar to the embodiment of FIG. 21. Like parts will be designated with like numbers. Thus, the salt conversion of the left-hand side of FIG. 22 is the same. The principle difference is that the aqueous solution 350, suitably deionized water, flows through a second electrode chamber containing the anode which then flows in line 360 back through electrode chamber 346. The cations, $K^+$ as illustrated, pass through barrier 344 as illustrated in FIG. 21.

Referring again to FIG. 22, barrier 362 separates bed 340 from anode 364 in the interior of electrode chamber 366. Barrier 362 is of the same type as barrier 344 but includes exchangeable ions of opposite charge. The principles of electrolytic operation using a cathode and an anode isolated from the ion exchange bed 340 is illustrated with respect to FIG. 2 of U.S. Pat. No. 6,027,643. The difference is that the bed 340 serves as a pH adjuster rather than a suppressor as in the patent.

Other electrolytic or non-electrolytic pH adjusters may be used which accomplish the purposes of the present invention of converting a weak acid salt to its conjugate acid.

All of the above systems can be used to generate other acids (e.g., sulfuric acid, methane sulfonic acid, acetic acid, etc.) or bases (e.g., of alkali metals and alkaline earth) as set forth in the above patents and applications and mixtures thereof to form salts. Further, the polarity of any of the base generators may be reversed to reverse the order of generation. Similarly, the order of flow through any acid or base generator in a combination of different generators may be reversed. All of the above patents and applications are incorporated herein by reference. In addition to being used as eluents in ion chromatography, the high purity salt, acid, and base solutions generated as described in this application may be used as eluents in liquid chromatography, and other chemical analysis applications such as titration, flow injection analysis, etc.

In order to further illustrate the present invention, the following specific examples are provided.

EXAMPLE 1

This example illustrates use of an eluent generator of the type illustrated in FIG. 2 to generate $K_2CO_3$ in ion chromatographic separation of anions.

A $K_2CO_3$ eluent generator of the type illustrated in FIG. 2 was constructed. An EGC-KOH generator cartridge (P/N 53986, Dionex Corporation, Sunnyvale, Calif.) was used as the cathode chamber, and an EGC-MSA generator cartridge (P/N 53987, Dionex Corporation) was first converted to the carbonate form and used as the anode chamber. The cathode chamber was connected to the anode chamber using a coupler (1 inch in internal diameter and 3 inch in length) made of polypropylene. This polypropylene coupler serves as the electrolyte chamber of the $K_2CO_3$ generator was filled with about 50 mL of 3.0 M $K_2CO_3$ solution. A Dionex EG40 Eluent Generator Module was used to supply the DC current to the anode and cathode of the eluent generator. The $K_2CO_3$ generator was operated in the flow direction of cathode chamber (KOH generation chamber) to anode chamber ($H_2CO_3$ generation chamber). FIG. 2 illustrates an ion chromatographic system using the $K_2CO_3$ eluent generator. A DX500 ion chromatographic system (Dionex Corporation) consisting of a GP40 pump, an injection valve and an AS9 HC separation column (4-mm ID×250-length) was used. A Dionex ASRS anion suppressor (P/N 53946) was used as the suppressor. A built-in power supply in a Dionex ED40 detector was used to supply 300 mA of DC current to the suppressor. A Dionex ED40 conductivity detector equipped with a flow-through conductivity cell was used as the detector. A Dionex PeakNet 5.0 computer workstation was used for instrument control, data collection and processing.

The operation of the $K_2CO_3$ eluent generator was evaluated by using it to generate a 9.0-mM $K_2CO_3$ eluent (the applied current was 29 mA) at 1.0 mL/min for separation of five common anions on a 4-mm AS9-HC column. FIG. 9 shows the chromatograms obtained using either 9 mM $K_2CO_3$ from a bottle prepared by the conventional method or 9 mM $K_2CO_3$ generated using the $K_2CO_3$ eluent generator. The chromatogram obtained using the $K_2CO_3$ eluent generator was similar to that obtained using 9.0 mM $K_2CO_3$ prepared conventionally. In another set of experiments, the system shown in FIG. 2 was operated continuously to perform the separation of five common anions for 15 days. FIG. 10 shows the stability of retention times of five common anions over 850 runs performed during the test. The percent RSDs for retention times of five anions ranged from 0.5 percent for fluoride to 2.2 percent for nitrate. These results indicate that the $K_2CO_3$ eluent generator is capable of generating the carbonate eluent reproducibly over an extended period of time.

In another set of experiments, the $K_2CO_3$ generator was programmed to generate a linear gradient of 0 to 30 mM $K_2CO_3$ at 1.0 mL/min, and the conductance of the $K_2CO_3$ eluent generator was measured. It was found that the device flow direction had an effect on the conductance profile of the $K_2CO_3$ generated. FIG. 11 shows the conductance profiles of a linear $K_2CO_3$ gradient (0 to 30 mM at 1.0 mL/min) obtained using the device in both flow directions. The flow direction of cathode chamber to anode chamber yielded a better linear gradient profile.

EXAMPLE 2

This example illustrates use of the same apparatus as Example 1 to generate a $K_2CO_3/KHCO_3$ eluent in ion chromatographic separation of anions.

A $K_2CO_3/KHCO_3$ generator cartridge was constructed using the same components that were used for the $K_2CO_3$ generator cartridge, as described in Example 1. The electrolyte chamber of the $K_2CO_3/KHCO_3$ eluent generator was filled with about 50 mL of 1.8 M $K_2CO_3$/1.7 M $KHCO_3$ solution. The flow direction was from the cathode chamber to the anode chamber. A Dionex EG40 Eluent Generator Module was used to supply the DC current to the anode and cathode of the eluent generator.

The performance of the $K_2CO_3/KHCO_3$ eluent generator was evaluated by using it to generate a 1.8 mM $K_2CO_3$/1.7 mM $KHCO_3$ eluent at 2.0 mL/min for separation of five common anions. An ion chromatography system identical to that used in Example 1 was used in the experiments except that a 4-mm AS4A SC column (4-mm ID×250-length) was used as the separation column. To generate 1.8 mM $K_2CO_3$/ 1.7 mM $KHCO_3$ eluent at 2.0 mL/min, a DC current of 8.4 mA was applied to the $K_2CO_3/KHCO_3$ eluent generator cartridge. It was assumed that carbonate and bicarbonate would migrate across the membranes in the anode chamber in a ratio similar to that in the electrolyte solution. FIG. 12 shows a representative chromatogram obtained using the device.

EXAMPLE 3

This example illustrates the use of an eluent generator of the type illustrated in FIG. 5 to generate a $K_2CO_3$ eluent in ion chromatographic separation of anions.

A potassium carbonate eluent generator of the type illustrated in FIG. 5 was constructed. An EGC-KOH cartridge (P/N 53986, Dionex Corporation, Sunnyvale, Calif.) was used as the KOH generator. The EGC-$H_2CO_3$ cartridge was constructed using the same components as those used in an EGC-MSA generator cartridge (P/N 53987, Dionex Corporation), except that the ion exchange connector was in the carbonate form. The electrolyte reservoir of the EGC-$H_2CO_3$ cartridge was filled with a solution of 3.0 M $K_2CO_3$. A Dionex EG40 Eluent Generator Module was used to supply and control the DC current (33 mA) to the anode and cathode of the EGC-$H_2CO_3$ cartridge. A Dionex SC20 DC power supply module (P/N 057755) was used to supply and control the DC current (29 mA) to the anode and cathode of the EGC-KOH cartridge. The other components of the ion chromatography system were the same as those described in Example 1. The operation of the eluent generator was evaluated by using it to generate a 9.0-mM $K_2CO_3$ eluent at 1.0 mL/min. FIG. 13 shows the separation of seven common anions on a 4-mm AS9-HC column (P/N 051786, Dionex Corporation) using the $K_2CO_3$ eluent generated.

EXAMPLE 4

This example illustrates the use of an eluent generator of the type illustrated in FIG. 5 to generate a $K_2CO_3/KHO_3$ eluent in ion chromatographic separation of anions.

A potassium carbonate eluent generator of the type illustrated in FIG. 5 was constructed. An EGC-KOH cartridge (P/N 53986, Dionex Corporation, Sunnyvale, Calif.) was used as the KOH generator. The EGC-$H_2CO_3$ cartridge was constructed using the same components as those used in an EGC-MSA generator cartridge (P/N 53987, Dionex Corporation), except that the ion exchange connector was in the carbonate form. The electrolyte reservoir of the EGC-$H_2CO_3$ cartridge was filled with a solution of 3.0 M $K_2CO_3$. A Dionex EG40 Eluent Generator Module was used to supply and control the DC current (17.4 mA) to the anode and cathode of the EGC-$H_2CO_3$ cartridge. A Dionex SC20 DC power supply module (P/N 057755, Dionex Corporation) was used to supply and control the DC current (15.4 mA) to the anode and cathode of the EGC-KOH cartridge. The other components of the ion chromatography system were the same as those described in Example 1. The operation of the eluent generator was evaluated by using it to generate an eluent of 3.5 mM $K_2CO_3$ and 1.0 mM $KHCO_3$ at 1.2 mL/min. FIG. 14 shows the separation of seven common anions on a 4-mm AS 14 column (P/N 046124, Dionex Corporation) using the $K_2CO_3/KHCO_3$ eluent generated.

EXAMPLE 5

In this example, the eluent generator of FIG. 16 is used in a typical ion chromatography system including the components downstream of the generator illustrated in FIG. 2. Specifically, seven ions were separated on a Dionex AS9 HC column using the 9 mM potassium carbonate generated by a device of FIG. 17. A DC current of 29 mA was applied to the carbonate generator to generate 9 mM $K_2CO_3$ at 1.0 mL/min. The results are shown in FIG. 19.

EXAMPLE 6

In this example, the apparatus of FIG. 21 is used. The $K_2CO_3$ solution in line 20 is at a concentration of 9 mM at 1.0 mL/min. flow rate. A DC current of 3.22 mA is applied to pH modifying device 341. To displace an amount of K+ ions equivalent to 2 mN $K^+$ at 1.0 mL/min. The resulting solution in line 354 contains 8.0 mM $K_2CO_3$ and 1.0 mM $KHCO_3$ at the same flow rate.

The invention claimed is:

1. A method of generating an acid and a base comprising the steps of:
   (a) providing a source of first ions adjacent an aqueous liquid in a first acid or base generation zone, said first ion source and first zone being separated by a first barrier substantially preventing liquid flow and transporting ions only of the same charge as said first ions,
   (b) providing a source of second ions of opposite charge to said first ions adjacent an aqueous liquid in a second acid or base generation zone, said second ion source and second zone being separated by a second barrier substantially preventing liquid flow and transporting ions only of the same charge as said second ions,
   (c) transporting ions of a first charge, positive or negative, across said first barrier by applying an electrical potential through said first zone to electrically charge the same with a charge opposite to said first charge and applying an electrical potential through said second zone to electrically charge the same with a charge opposite to the charge of said first zone so that hydroxide ions are generated in one of said first or second zones and hydronium ions are generated in the other of said first and second zones and ions of opposite charge to the electrical charges of said first and second zones, respectively, are transported across said first and second barriers to combine with said hydroxide or hydronium ions in said first and second zones to generate an acid-containing aqueous solution in one of said first or second zones and a base-containing aqueous solution in the other one,
   (d) mixing said generated acid-containing and base-containing aqueous solutions to form a salt-containing aqueous solution, and
   (e) flowing said salt-containing aqueous solution as a chromatography eluent together with a sample analyte solution through chromatography separation medium to chromatographically separate the analytes.

2. The method of claim 1 in which said first and second zones are in separate first and second chambers, respectively.

3. The method of claim 1 in which the first and second ion sources comprise a salt solution of said first and second ions.

4. The method of claim 3 in which said salt solution is in one chamber.

5. The method of claim 3 in which said sources of said first and second ion comprise a common reservoir of said salt solution disposed between said first and second barriers.

6. The method of claim 1 in which said first and second barriers are part of a continuous barrier.

7. The method of claim 1 in which said first and second barriers are independent of each other.

8. The method of claim 1 in which said electrical potential is applied between first and second electrodes of opposite charge in electrical communication with said first and second zones, respectively.

9. The method of claim 8 in which said first and second electrodes are in contact with said first and second zones, respectively.

10. The method of claim 8 in which said first electrode is in contact with said first ion source and said second electrode is in contact with said first zone.

11. The method of claim 1 in which said acid-containing aqueous solution flows as a chromatography eluent together with a sample analyte solution through chromatography separation medium to chromatographically separate the analytes.

12. The method of claim 1 in which said base-containing aqueous solution flows as a chromatography eluent together with a sample analyte solution through chromatography separation medium to chromatographically separate the analytes.

13. The method of claim 1 in which an aqueous liquid flows through said first chamber and carries the acid or base generated therein to said second chamber wherein said mixing takes place.

14. The method of claim 1 in which said first and second ion sources comprise first and second substantially non-flowing solutions of said first and second ions, respectively.

15. The method of claim 1 in which said first and second ion sources comprise flowing solutions.

16. The method of claim 1 in which said first and second ion sources are selected from the group consisting of aqueous solutions of an acid, a base or a salt.

17. The method of claim 1 in which said first and second zones comprise ion exchange medium of opposite charge adjacent to said first and second barriers.

18. The method of claim 1 in which said first and second ion sources are contained in separate first and second reservoirs, respectively.

19. The method of claim 18 in which one of said first or second ion source reservoirs comprises a substantially non-flowing solution comprising said first or second ions and the other of said first or second ion source reservoirs comprises liquid flow-through ion exchange medium having exchangeable ions comprising the other of said first and second ions.

20. The method of claim 1 in which said first ion source comprises first reservoir ion exchange flow-through medium disposed in a first reservoir and having exchangeable first ions and in which a solution of said first ions flows through said first reservoir ion exchange medium.

21. The method of claim 20 in which an analyte sample and said salt-containing aqueous solution flow through chromatography separation medium and then through a chromatography effluent flow channel of a membrane suppressor separated by a suppressor membrane from a regenerant flow channel, said method further comprising forming a solution comprising said first ions in said regenerant flow channel which flows through said first reservoir ion exchange resin.

22. The method of claim 19 in which said second ion source comprises ion exchange medium disposed in a second reservoir, and the ion solution formed in said regenerant flow channel is a salt of said first and second ions, said method further comprising flowing said formed salt through said second reservoir.

23. The method of claim 22 in which said electrical potential is applied across said second reservoir ion exchange medium, said method further comprising flowing said formed salt solution past an electrode adjacent the outlet of second ion exchange medium of opposite charge to the charge of said second chamber so that said first ions electromigrate toward said electrode.

24. The method of claim 23 in which the first ion-containing solution flowing out of said first reservoir flows through said second reservoir ion exchange medium having exchange ions of the same charge as said first ion solution in a first reservoir comprising said first ion source.

25. The method of claim 1 in which said first ion source comprises a first ion source reservoir and said second ion source comprises a second ion source reservoir, said method further comprising:
(f) flowing said formed salt-containing solution as an eluent with analyte sample through chromatographic separation medium, and
g) flowing the chromatography effluent through a suppressor comprising ion exchange medium having exchangeable ions of the same charge as said first ions.

26. The method of claim 1 in which a first electrical potential is applied between a first pair of electrodes of opposite charge, one of which is in electrical communication with said first reservoir and the other of which is in electrical communication with said first zone, and a second electrical potential is applied between a second pair of electrodes of opposite charge, one of which is in electrical communication with said second reservoir and the other of which is in electrical communication with said second zone.

27. The method of claim 1 further comprising the step of (f) electrolytically modifying the pH value of said salt-containing solution.

28. The method of claim 27 in which the anion of the salt in said salt-containing solution is a weak acid.

29. The method of claim 28 in which said salt-containing solution is an alkali metal carbonate and said electrolytically modified salt-containing solution comprises an alkali metal carbonate/bicarbonate solution.

* * * * *